(12) United States Patent
Roger

(10) Patent No.: US 8,821,500 B2
(45) Date of Patent: Sep. 2, 2014

(54) FEMORAL CUTTING BLOCK

(75) Inventor: Christopher Abee Roger, Waldwick, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1775 days.

(21) Appl. No.: 11/642,355

(22) Filed: Dec. 20, 2006

(65) Prior Publication Data

US 2008/0154268 A1    Jun. 26, 2008

(51) Int. Cl.
*A61B 17/58* (2006.01)
*A61B 17/15* (2006.01)

(52) U.S. Cl.
CPC .................................... *A61B 17/155* (2013.01)
USPC ......................................................... 606/88

(58) Field of Classification Search
USPC .................................................... 606/87–89
See application file for complete search history.

(56) References Cited

U.S. PATENT DOCUMENTS

| | | | | |
|---|---|---|---|---|
| 4,421,112 A | * | 12/1983 | Mains et al. | 606/88 |
| 4,703,751 A | * | 11/1987 | Pohl | 606/62 |
| 4,718,413 A | * | 1/1988 | Johnson | 606/82 |
| 4,892,093 A | | 1/1990 | Zarnowski et al. | |
| 4,926,847 A | * | 5/1990 | Luckman | 606/88 |
| 5,129,909 A | | 7/1992 | Sutherland | |
| 5,417,694 A | * | 5/1995 | Marik et al. | 606/88 |
| 5,454,816 A | | 10/1995 | Ashby | |
| 5,520,695 A | * | 5/1996 | Luckman | 606/88 |
| 5,593,411 A | * | 1/1997 | Stalcup et al. | 606/88 |
| 5,683,398 A | * | 11/1997 | Carls et al. | 606/89 |
| 5,709,689 A | * | 1/1998 | Ferrante et al. | 606/86 R |
| 5,817,097 A | * | 10/1998 | Howard et al. | 606/87 |
| 5,885,296 A | | 3/1999 | Masini | |
| 5,925,049 A | | 7/1999 | Gustilo et al. | |
| 6,007,537 A | * | 12/1999 | Burkinshaw et al. | 606/66 |
| 6,010,508 A | * | 1/2000 | Bradley | 606/86 R |
| 6,013,081 A | | 1/2000 | Burkinshaw et al. | |
| 6,086,593 A | * | 7/2000 | Bonutti | 606/87 |
| 6,099,531 A | * | 8/2000 | Bonutti | 606/87 |
| 6,440,140 B2 | | 8/2002 | Bullivant et al. | |
| 6,458,135 B1 | | 10/2002 | Harwin et al. | |
| 6,558,391 B2 | | 5/2003 | Axelson, Jr. et al. | |
| 6,685,711 B2 | | 2/2004 | Axelson, Jr. et al. | |
| 6,702,821 B2 | * | 3/2004 | Bonutti | 606/88 |
| 6,740,092 B2 | | 5/2004 | Lombardo et al. | |
| 6,962,593 B2 | | 11/2005 | Sanford et al. | |
| 7,081,137 B1 | | 7/2006 | Servidio | |
| 7,621,919 B2 | | 11/2009 | Williams, III et al. | |
| 7,666,187 B2 | | 2/2010 | Axelson, Jr. et al. | |
| 7,837,690 B2 | | 11/2010 | Metzger | |
| 2002/0052606 A1 | * | 5/2002 | Bonutti | 606/88 |
| 2003/0018338 A1 | | 1/2003 | Axelson et al. | |
| 2004/0087960 A1 | * | 5/2004 | Kinnett | 606/88 |
| 2005/0154394 A1 | * | 7/2005 | Michalowicz | 606/87 |

(Continued)

*Primary Examiner* — Christian Sevilla
(74) *Attorney, Agent, or Firm* — Lerner, David, Littenberg, Krumholz & Mentlik, LLP

(57) ABSTRACT

A cutting block assembly comprising first and second interlocking blocks for resecting a distal femur. The first block has a first surface for providing a guiding surface for making an anterior chamfer cut on the femur and a second surface for providing a guiding surface for making a posterior chamfer cut on the femur. The second block is adapted to detachably couple to the first block. The second block has a first surface for providing a guiding surface for making an anterior cut on the femur and a second surface for providing a guiding surface for making a posterior cut on the femur.

20 Claims, 33 Drawing Sheets

(56) References Cited

U.S. PATENT DOCUMENTS

| | | |
|---|---|---|
| 2005/0228393 A1 | 10/2005 | Williams et al. |
| 2005/0240195 A1 | 10/2005 | Axelson et al. |
| 2005/0273113 A1 | 12/2005 | Kuczynski |
| 2006/0123962 A1* | 6/2006 | Fontaine .................. 83/446 |
| 2006/0142774 A1 | 6/2006 | Metzger |
| 2008/0015602 A1 | 1/2008 | Axelson |

* cited by examiner

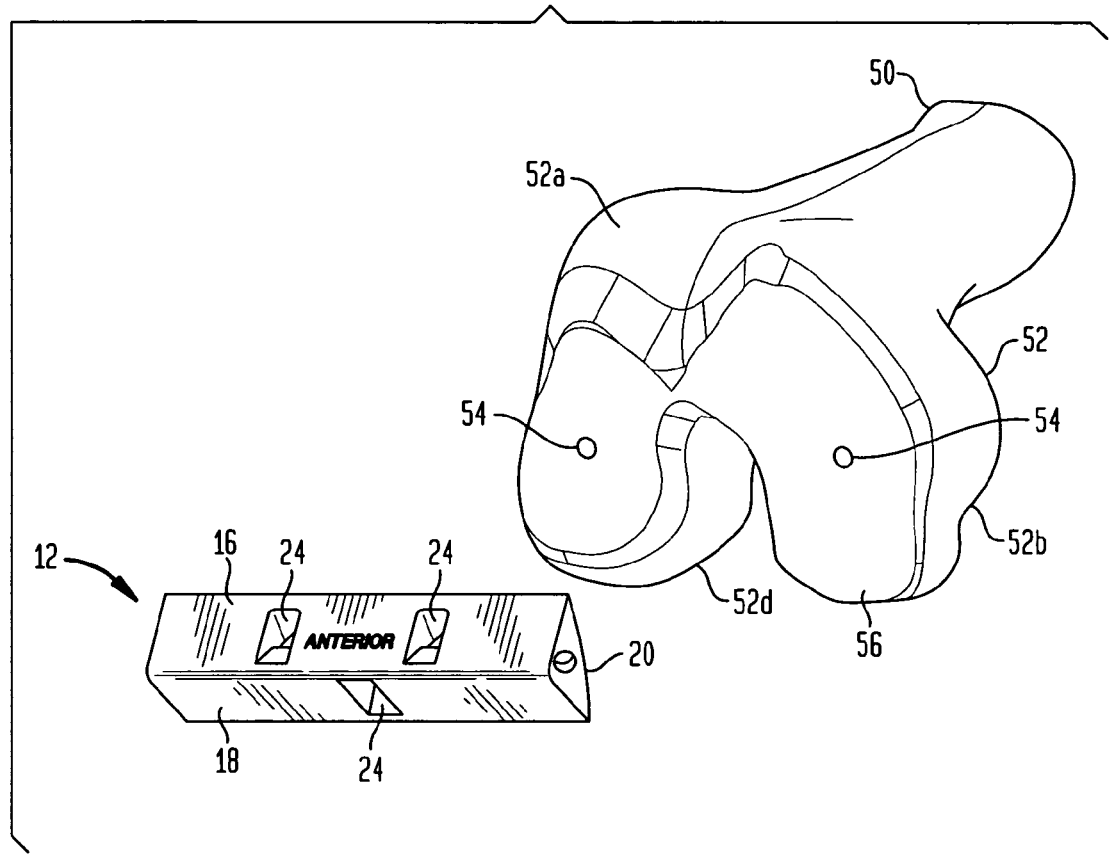

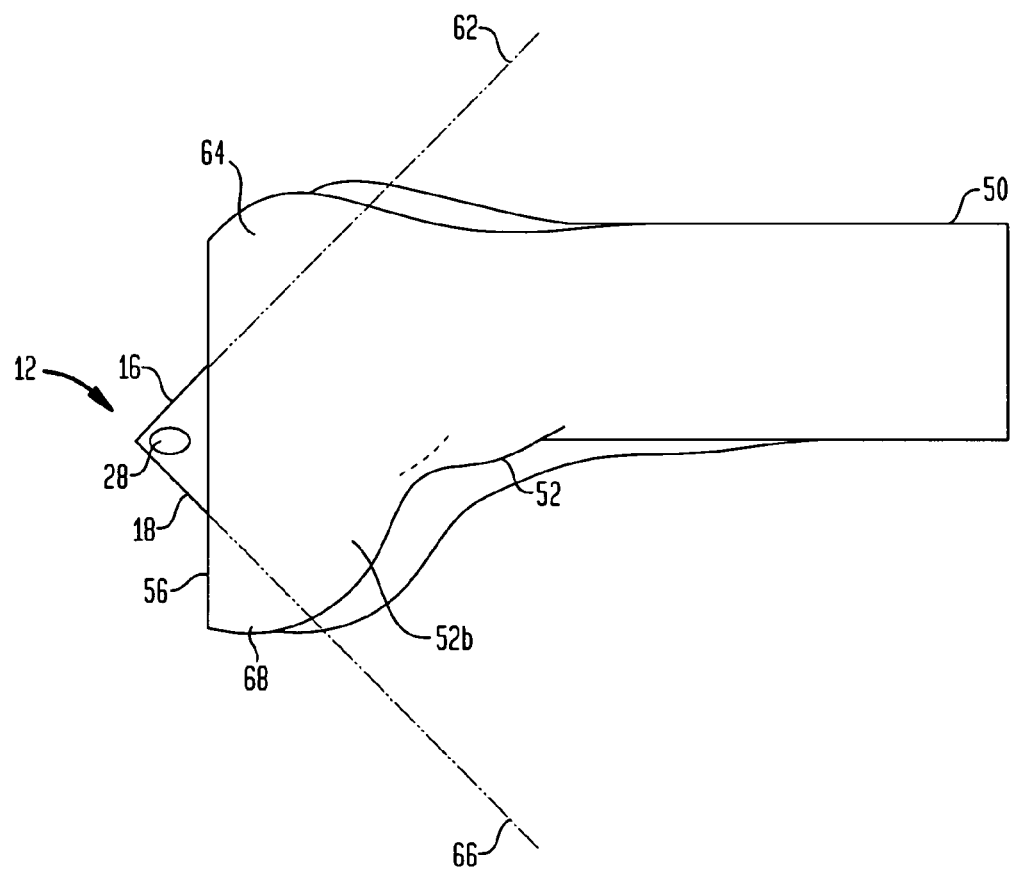

FEMORAL CUTTING BLOCK

BACKGROUND OF THE INVENTION

The present application relates generally to the implant of prosthetic joints and pertains, more specifically, to the preparation of the distal femur for the implantation of a femoral knee prosthesis, utilizing a femoral cutting block to assist in establishing the surfaces necessary for locating and securing the prosthesis in place on the femur.

The implant of a prosthetic knee joint requires that the distal femur be prepared to receive the femoral component of the knee prosthesis by cutting the bone of the femur to establish accurately located surfaces. Upon implantation, the femoral component will rest on these surfaces. As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Various cutting blocks are available to the surgeon for assisting in guiding a saw blade to make the femoral cuts which establish the desired surfaces. These guides usually have guide surfaces for making four resections and are located and secured on the distal femur, upon an already resected transverse surface on the distal femur. Typically, surfaces are provided for guiding the saw blade during the execution of an axially directed anterior femoral cut, an axially directed posterior femoral cut, an anterior chamfer and a posterior chamfer, all specifically related to the size of the femoral knee prosthesis to be implanted and to the position and orientation of the femoral knee prosthesis on the distal femur. A four-in-one cutting block is a single cutting block for making the four cuts. A four-in-two cutting block comprises two separate blocks for making the four cuts. However, such conventional cutting blocks may exhibit various disadvantages. For example, the two blocks of a conventional four-in-two cutting block are used separately and do not interlock to each other. That is, the first block is used making a first set of cuts comprising the anterior and posterior chamfer cuts and the second block is used for making a second set of cuts comprising the anterior and posterior cuts. The first set of cuts is loosely correlated to the second set of cuts which may decrease the accuracy of the cuts. In addition, these cutting blocks are made of metal which may increase the cost of manufacture. Moreover, because of the high cost of such blocks, they are typically reused for additional surgical procedures. However, this may require sterilization of the blocks which may be costly and inconvenient.

SUMMARY OF THE INVENTION

The present application provides a cutting block that may help overcome some of the above-mentioned disadvantages. The cutting block of the present application is a four-in-two (4-in-2) cutting block assembly which may improve the accuracy in the preparation of the distal femur for the implantation of a knee prosthesis. The cutting block assembly comprises a first block for making the anterior and posterior chamfer cuts and a second block for making the anterior and posterior cuts. The first and second blocks interlock which helps correlate the four cuts and improve the accuracy of the cuts. The second block includes extended cutting surfaces which may further help improve the accuracy of the anterior and posterior cuts. In addition, the second block provides a visual indication of the accuracy of the anterior and posterior chamfer cuts before the anterior and posterior cuts are made. Moreover, the cutting block can be made of polymeric material which may help reduce the cost of making the block. In addition, because polymeric material is relatively lightweight compared to metal, the cutting block may be relatively lightweight which may improve the handling of the cutting block during a surgical procedure.

In one aspect of the present application, disclosed is a cutting block assembly comprising interlocking first and second blocks for resecting a distal femur. The first block has a first surface for providing a guiding surface for making an anterior chamfer cut on the femur and a second surface for providing a guiding surface for making a posterior chamfer cut on the femur. The second block is adapted to detachably couple to the first block. The second block has a first surface for providing a guiding surface for making an anterior cut on the femur and a second surface for providing a guiding surface for making a posterior cut on the femur.

In another aspect of the present application, disclosed is a method of resecting a distal femur. The method includes attaching a first block to the distal femur, the first block having a first surface providing a guiding surface for making an anterior chamfer cut on the femur, a second surface providing a guiding surface for making a posterior chamfer cut on the femur, and making anterior and posterior chamfer cuts on the distal femur. The method further includes attaching a second block to the first block, the second block having a first surface providing a guiding surface for making an anterior cut on the femur, and a second surface providing a guiding surface for making a posterior cut on the femur, and making anterior and posterior cuts on the distal femur.

In yet another aspect of the present application, disclosed is a method of resecting a distal femur. The method includes attaching a first block to the distal femur, the first block having a first surface providing a guiding surface for making an anterior chamfer cut on the femur, a second surface providing a guiding surface for making a posterior chamfer cut on the femur. The method further includes attaching a second block to the first block, the second block having a first surface providing a guiding surface for making an anterior cut on the femur, and a second surface providing a guiding surface for making a posterior cut on the femur. The method further includes making anterior and posterior cuts on the distal femur, detaching the second block from the first block, and making anterior and posterior chamfer cuts on the distal femur.

BRIEF DESCRIPTION OF THE DRAWINGS

FIG. 9A is an isometric view and FIG. 9B is a medial view showing the first block of the cutting block of FIGS. 1-7 being attached to the distal femur of FIGS. 8A-8B.

FIG. 10A is an isometric view and FIG. 10B is a medial view showing the first block attached to the distal femur of FIGS. 9A-9B in preparation for making anterior and posterior chamfer cuts on the surface of the distal femur.

DETAILED DESCRIPTION

Figure 1:
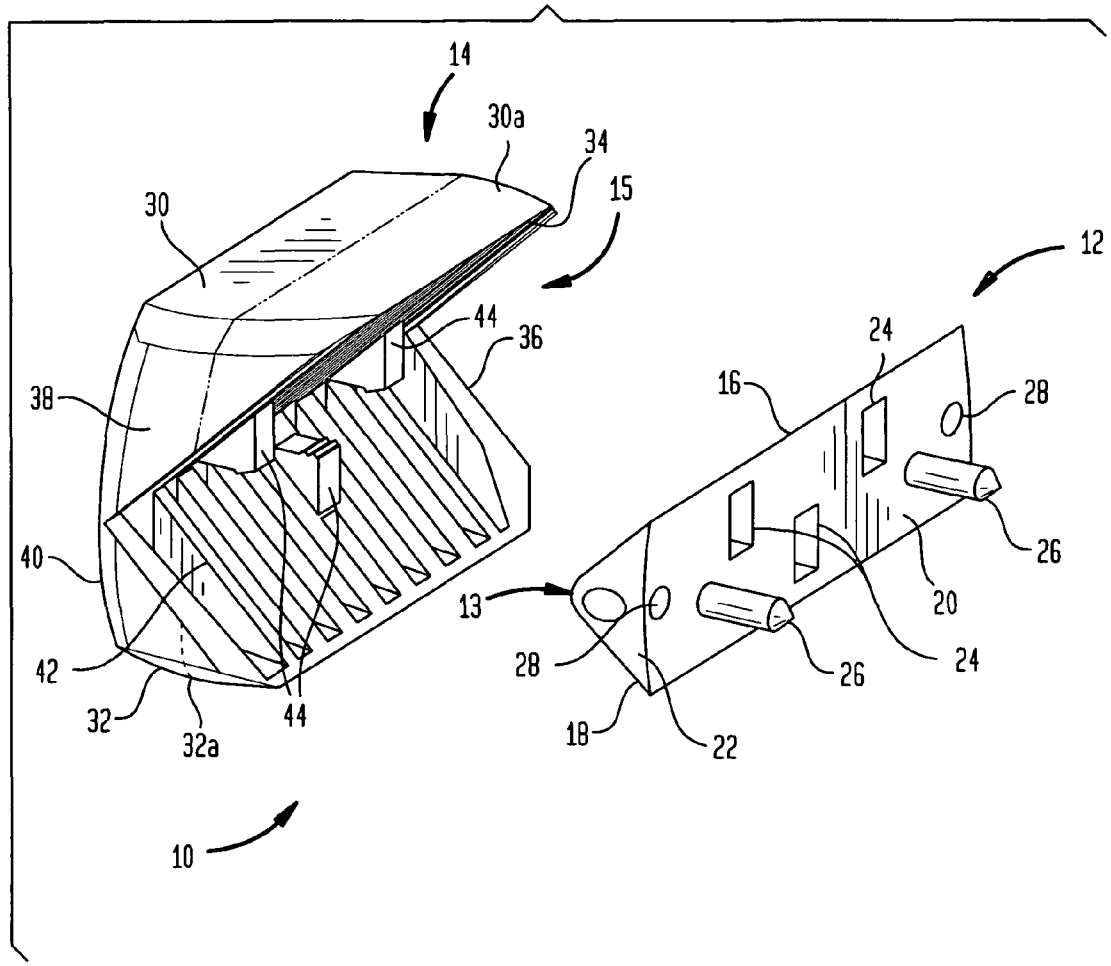
FIG. 1 is an isometric view of the bone cutting blocks in an un-assembled configuration, in accordance with an embodiment of the present application.
Figure 2:
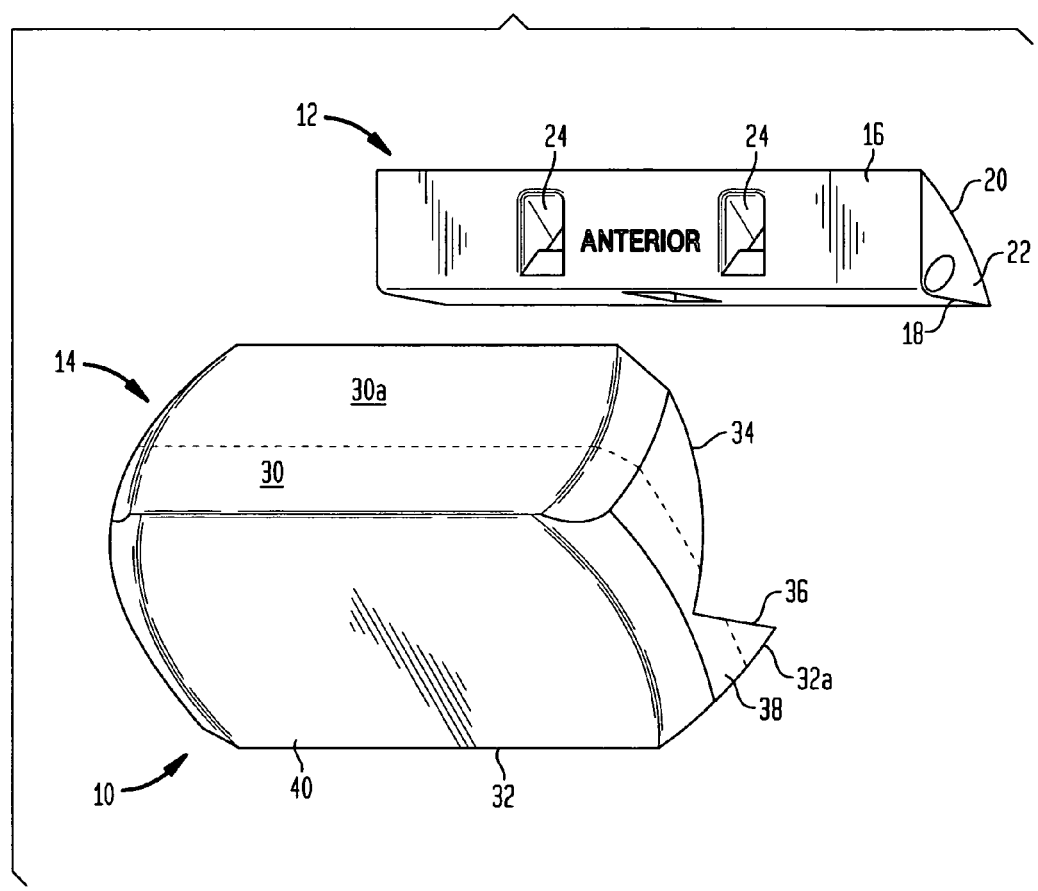
FIG. 2 is an isometric view of the cutting blocks of FIG. 1 from a different angle.

Referring to FIGS. 1-7, shown is a cutting block assembly generally denoted as 10 comprising a first block 12 capable of interlocking with a second block 14 to form a four-in-two (4-in-2) cutting block for resecting a portion of a bone such as a distal femur. Referring to FIGS. 1-2, the first block 12 is a generally triangular shaped block forming an anterior-chamfer cutting surface 16, a posterior-chamfer cutting surface 18, a contact surface 20 and side surfaces 22. The anterior-chamfer cutting surface 16 provides a guiding surface for making an anterior-chamfer cut on a femur (not shown). The posterior-chamfer cutting surface 18 provides a guiding surface for making a posterior-chamfer cut on the femur. The contact surface 20 includes protrusions 26 adapted to fit into holes in the distal femur to detachably couple the first block 12 to the distal resected surface of a distal femur (not shown), as explained below in further detail. In one embodiment, the protrusions 26 are shown as cylindrical posts but can have other shapes such as square. In one embodiment, the first block 12 also may include angled pin holes 28 extending outwardly from the contact surface 20 to the side surfaces 22. The pin holes 28 are adapted to receive pins (not shown) to more firmly secure the first block 12 to the distal resected surface of the distal femur. The cutting surfaces 16, 18 of the first block 12 form a generally V-shaped portion 13 for coupling to the second block 14, as explained below.

The second block 14 is a generally trapezoidal shaped block with V-shaped portion 15 sized to receive the V-shaped portion 13 of the first block 12. The second block 14 forms an anterior cutting surface 30, a posterior cutting surface 32, contact surfaces 34, 36 and side surfaces 38. The anterior cutting surface 30 provides a guiding surface for making an anterior cut on the femur. The posterior cutting surface 32 provides a guiding surface for making a posterior cut on the femur. The contact surfaces 34, 36 of the second block 14 form the generally V-shaped open-faced portion or channel 15 which is complementary to the generally V-shaped portion 13 formed by the surfaces 16, 18 of the first block 12. In this manner, as explained above, the portion 13 of the first block 12 is capable of fitting within the portion 15 of the second block 14.

One possible feature of the cutting block assembly 10 is an interlocking mechanism for detachably securing the blocks 12, 14 to each other. In a preferred embodiment, the interlocking feature is a slidable coupling mechanism comprising holes 24 of the first block 12 adapted to receive protrusions 44 of the second block 14. Two protrusions 44 extend outwardly from the surface 34 of the second block 14 and one protrusion 44 extends outwardly from the surface 36. In a complementary manner, two holes 24 extend through the surface 16 of the first block 12 and one hole 24 extends through the surface 18 of the first block. The protrusions are adapted to slide into and fit within the holes 24 to form an interlocking feature to detachably couple or interlock the first block 12 to the second block 14. Such an arrangement may provide various advantages. For example, as explained above, the first block 12 provides for anterior and posterior chamfer cuts and the second block 14 provides for anterior and posterior cuts. By using the interlocking feature to interlock the first block 12 with the second block 14, the cutting block assembly 10 allows the four distal femur cuts (anterior-chamfer, posterior-chamfer, anterior, posterior) to be tightly correlated to each other which may help increase the accuracy of the cuts.

Figure 7:
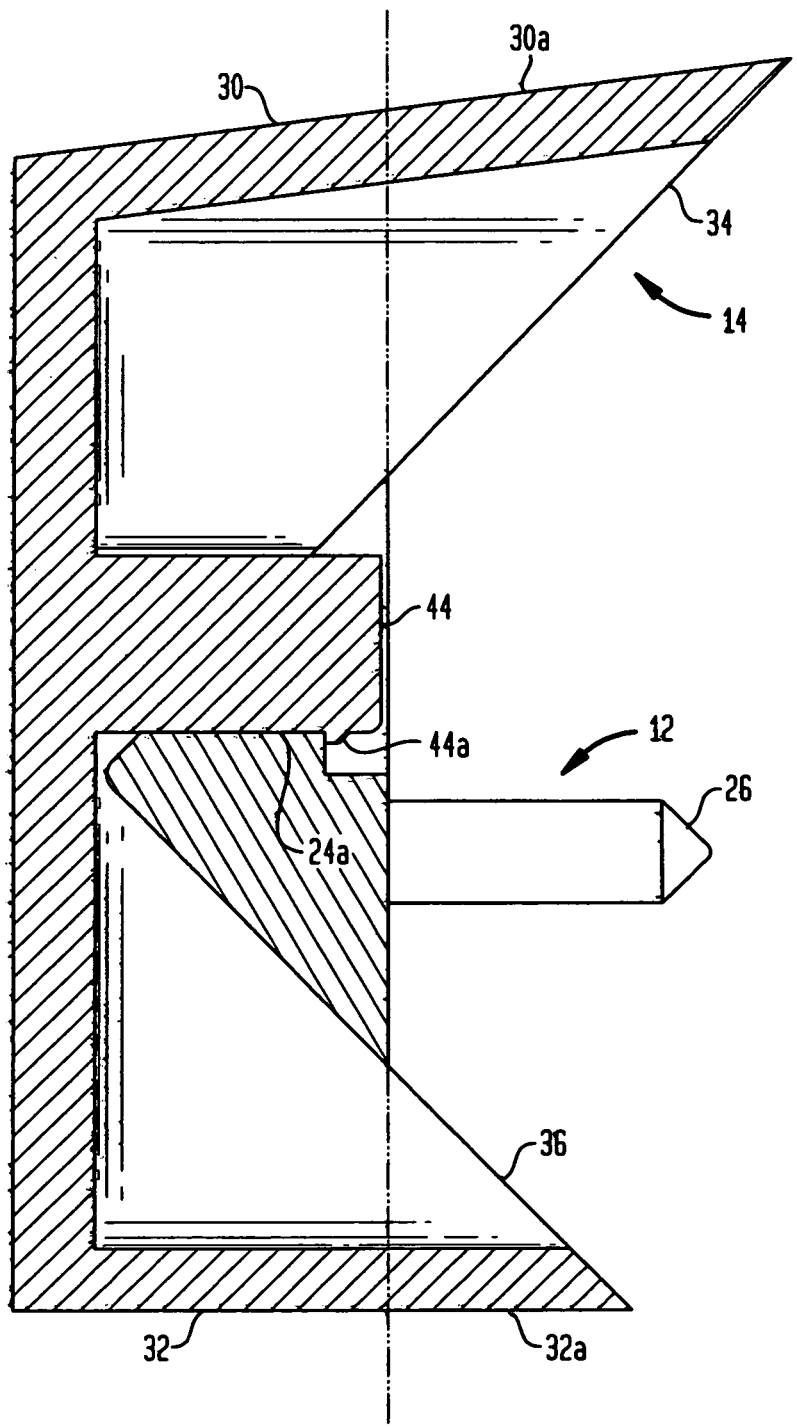
FIG. 7 is a detailed cross-sectional view of the cutting block assembly of FIG. 5B taken along lines A-A.

Another possible feature of the cutting block assembly 10 is that it provides a mechanism to verify the accuracy of the posterior and anterior chamfer cuts before the anterior and posterior cuts are made. For example, in one embodiment, the second block 14 includes extended portions 30a, 32a which extend beyond the contact surface 20 and cutting surfaces 16, 18 of the first block 12, as best shown in FIG. 7. The extended portions 30a, 32a include extended portions of contact surfaces 34, 36, respectively, and extended portions of cutting surfaces 30, 32, respectively. As explained below in detail, because the extended cutting surfaces 30, 32, which are part of extended portions 30a, 32a, provide increased cutting surface area for making the anterior and posterior cuts which may help improve the accuracy of the anterior and posterior cuts. In addition, the contact surfaces 34, 36, which are part of portions 30a, 32a, extend onto the chamfer cuts which may allow a user to verify the anterior and posterior chamfer cuts made with the first block before making the anterior and posteriors cuts with the second block.

Another possible feature of the cutting block assembly is that it can be made of relatively lightweight material which may provide various advantages. In one embodiment, the blocks 12, 14 are made of a polymeric material such as plastic which may help reduce the complexity and cost of manufacturing the block. Moreover, because the blocks are made of a polymeric material, the blocks can be discarded after being used instead of having to sterilize the blocks for subsequent use. However, the blocks 12, 14 can be made of other materials, such as metal, or other materials well known to one skilled in the art. In a preferred embodiment, the cutting surfaces 16, 18, 30, 32 are generally planar and smooth. In another embodiment, the surfaces 16, 18, 30, 32 can be non-smooth with grooves or ridges on the surfaces. In a preferred embodiment, the contact surfaces 34, 36 of the second block 14 are formed with ribs 42 extending into the interior of the block which may help reduce the amount of material and thus improve manufacturability and reduce the cost of manufacture. In addition, the use of less material and/or polymeric material may help make the cutting block more lightweight which may make the cutting block easier to use or manipulate during a surgical procedure.

Another possible feature of the cutting block assembly is that it provides a "keyed" mechanism to help ensure that the blocks are interlocked in a proper manner. In one embodiment, the number and arrangement of the protrusions 44 and holes 24 provide a locking mechanism which requires the blocks 12, 14 to be oriented and coupled to each other in only a single configuration. The first block 12 includes two holes 24 disposed over a single hole 24. In a complementary manner, the second block 14 includes two protrusions 44 disposed over a single protrusion. In this manner, the blocks 12, 14 can be coupled to each other in only one orientation. That is, the anterior surfaces 16, 30 are required to be aligned to each other and the posterior surfaces 18, 32 are required to be aligned to each other. This feature may help reduce the possibility of error during a surgical procedure. However, the number, size and arrangement of the protrusions 44 and holes 24 can be implemented in other ways. For example, the arrangement can be reversed, with one protrusion disposed over the two protrusions and the holes 24 configured in a similar manner.

Figure 3:
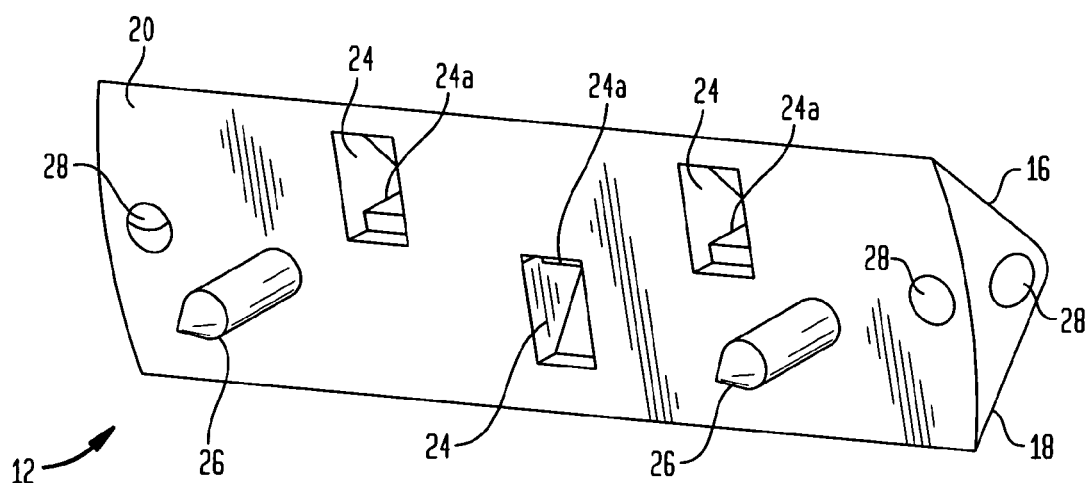
FIG. 3 is a detailed isometric view of a first block of the cutting block assembly of FIG. 1.
Figure 4:
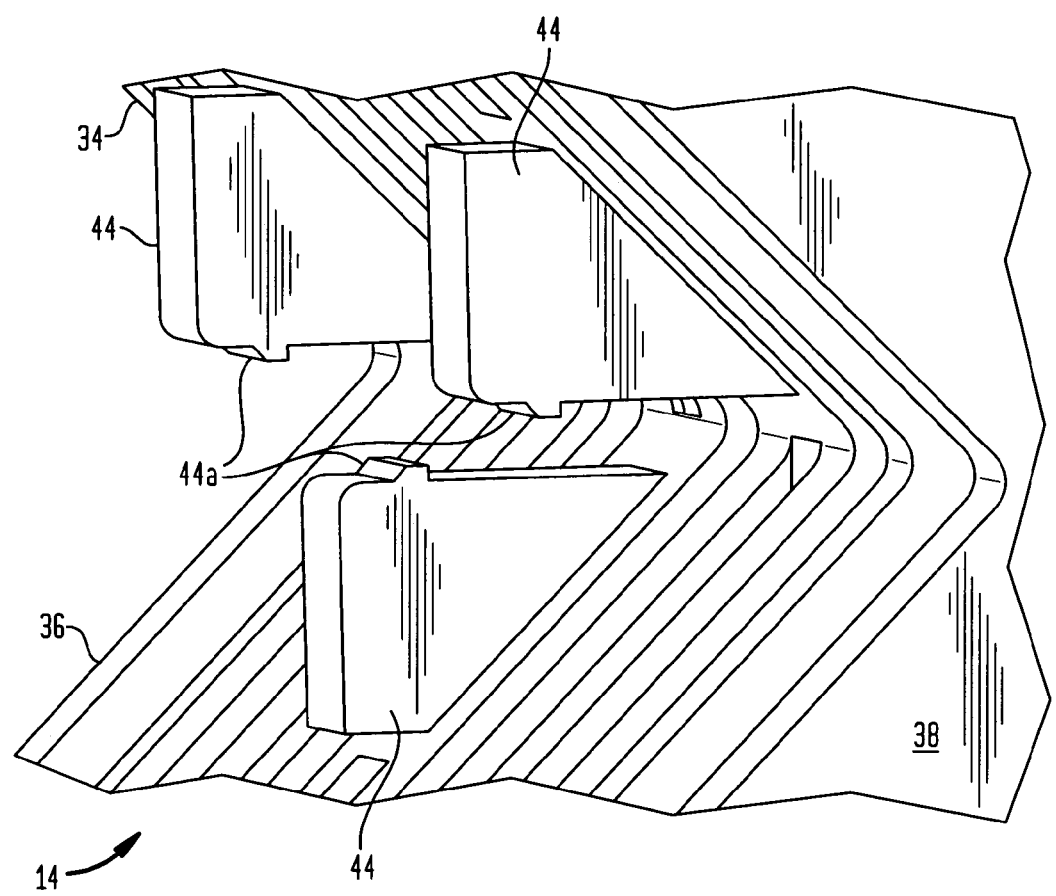
FIG. 4 is a detailed partial isometric view of a second block of the cutting block assembly of FIG. 1.
Figure 5A:
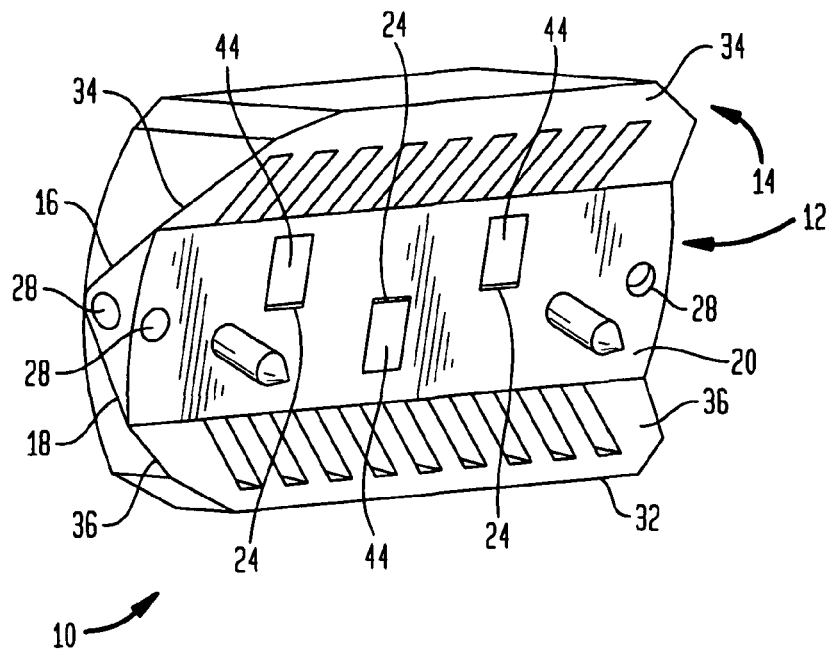
FIG. 5A is an isometric view of the cutting block assembly of FIG. 1 in shown an assembled configuration.
Figure 5B:
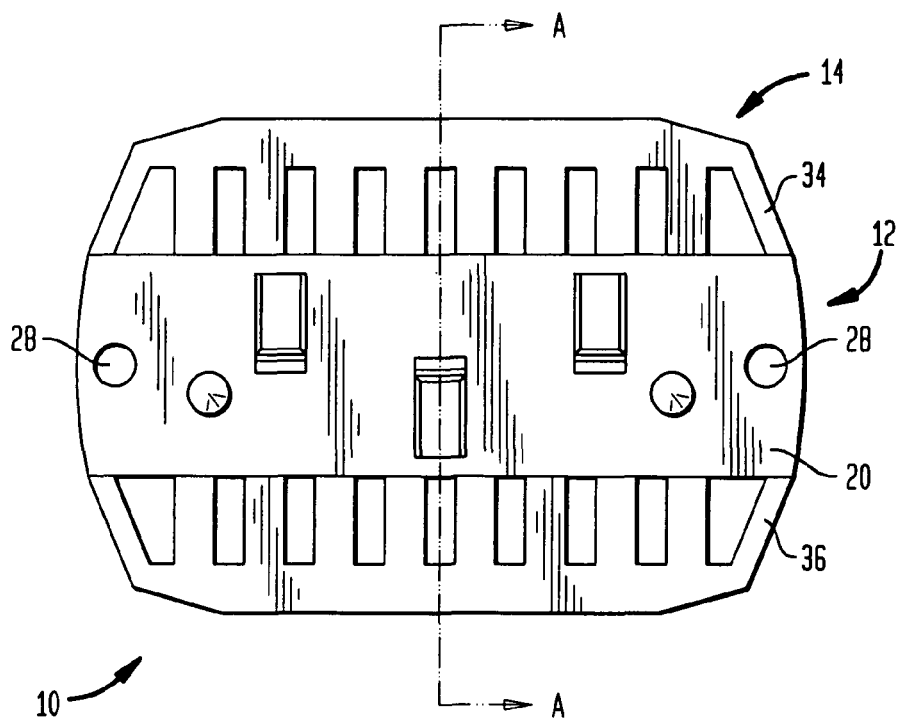
FIG. 5B is a rear view of the second block of FIG. 5A.
Figure 6:
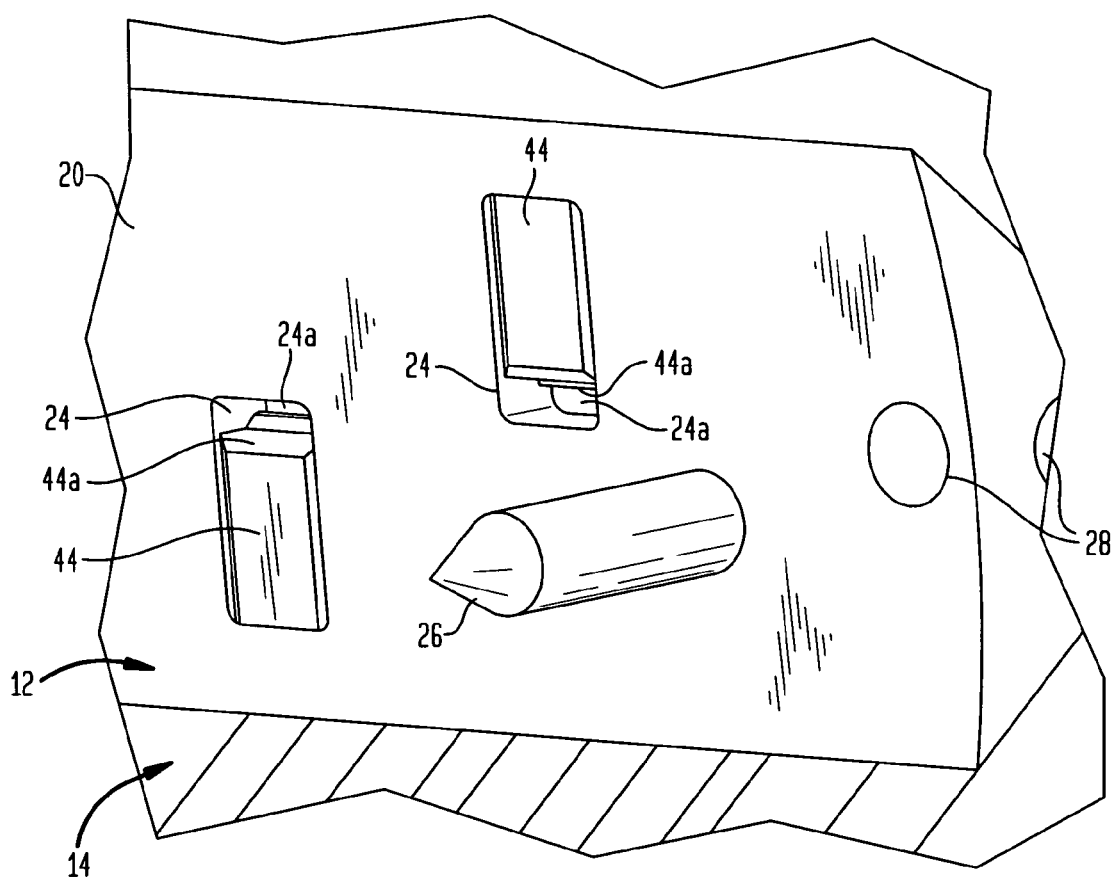
FIG. 6 is a detailed partial isometric view of the cutting block assembly of FIG. 5B.

Referring to FIGS. 3 and 4, shown are detailed views of the first block 12 and second block 14 respectively of FIGS. 1-2. As explained above, the protrusions 44 of the second block 14 are adapted to fit within the holes 24 of the first block 12 to form an interlocking feature to detachably couple or interlock the blocks 12, 14 to each other. The protrusions 44 and the corresponding holes 24 are shown as generally square shaped but can have other shapes, such as cylindrical, as long as they are complementary to provide a relatively secure interlock between the blocks. The protrusions 44 have generally square shaped ramps 44a on bottom surfaces of the protrusions. In a complementary manner, the holes 24 have generally square shaped ramps 24a on bottom surfaces of the holes. The protrusions 44 are slightly yieldable to accommodate the ramps 24a of the holes, as explained below.

FIGS. 4, 5A, 5B, and 6 show detailed views of the first block 12 and second block 14 of FIG. 1 in an assembled configuration. To assemble the blocks 12, 14 to form assembly 10, the blocks 12, 14 are advanced toward each other to permit the protrusions 44 of the second block 14 to be inserted into the holes 24 of the first block 12. The blocks 12, 14 are further advanced toward each other such that the ridges 44a of the second block 14 contact the ramps 24a of the first block 12. As the blocks 12, 14 are further advanced toward each other, the protrusions 44 yield upward and away from the ramps 24a and the ridges 44a pass beyond the surface of the ramps 24a and return to their original position. Once the ridges 44a are positioned behind the surfaces of the ramps 24a, the protrusions 44 are held in place in the holes 24 to provide a secure detachable coupling or interlock between the blocks 12, 14. To detach the blocks 12, 14 from each other, the blocks are moved away from each other with sufficient force to cause the ridges 44a to slide over and away from the ramps 24a thereby freeing the blocks from each other.

Figure 8A:
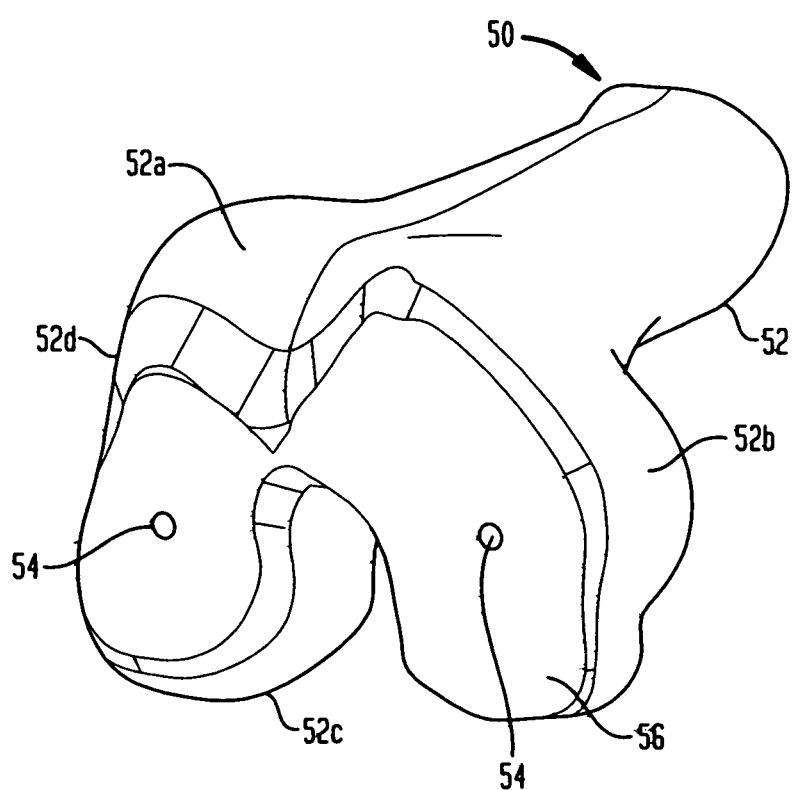
FIG. 8A is an isometric view and FIG. 8B is a medial view of a distal femur after a distal cut has been made on the surface of the distal femur.
Figure 8B:
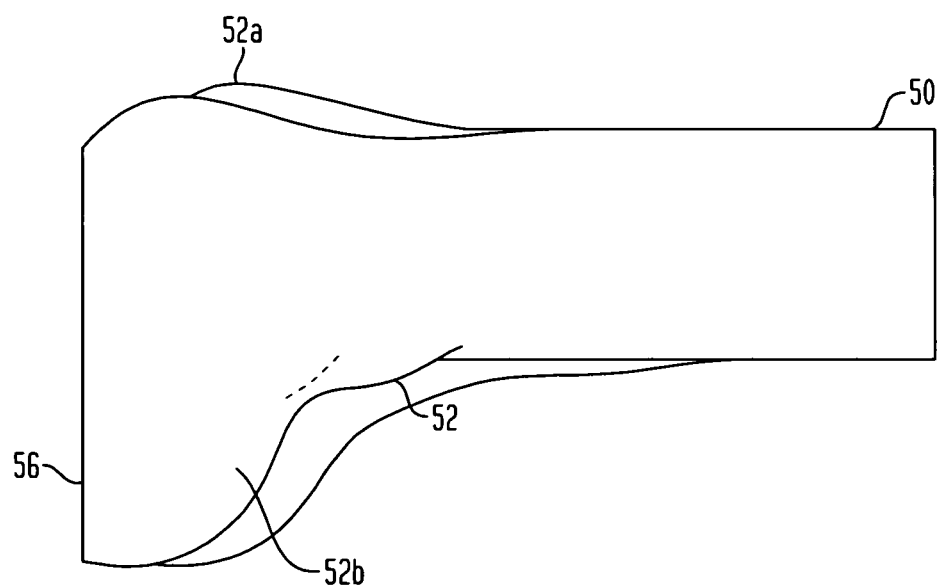

Referring to FIGS. 8A-8B to 14A-14B, a description is provided of a surgical procedure for resecting a distal femur 52 of a femur bone 50 using the cutting block assembly 10 of FIGS. 1-7 in accordance with an embodiment of the present application. Referring to FIGS. 8A-8B, the distal femur 52 has an anterior portion 52a, a medial portion 52b, a posterior portion 52c, and a lateral portion 52d. In an initial step of the surgical procedure, a distal cut is made which involves the resection or removal of a distal bone portion (not shown) from the distal femur 52 leaving behind a generally flat resected distal surface 56. A cutting device (not shown) can be used to remove the distal bone portion using conventional techniques. The cutting device can be a bone cutter such as an oscillating saw or other bone cutting device well-known to one skilled in the art. Once the distal cut has been made, pilot holes 54 can be drilled into the distal surface 56 in precise location and orientation as known to one skilled in the art to accommodate the protrusions 26 of the first block 12 as shown in FIGS. 9A-9B and described below.

Figure 9B:
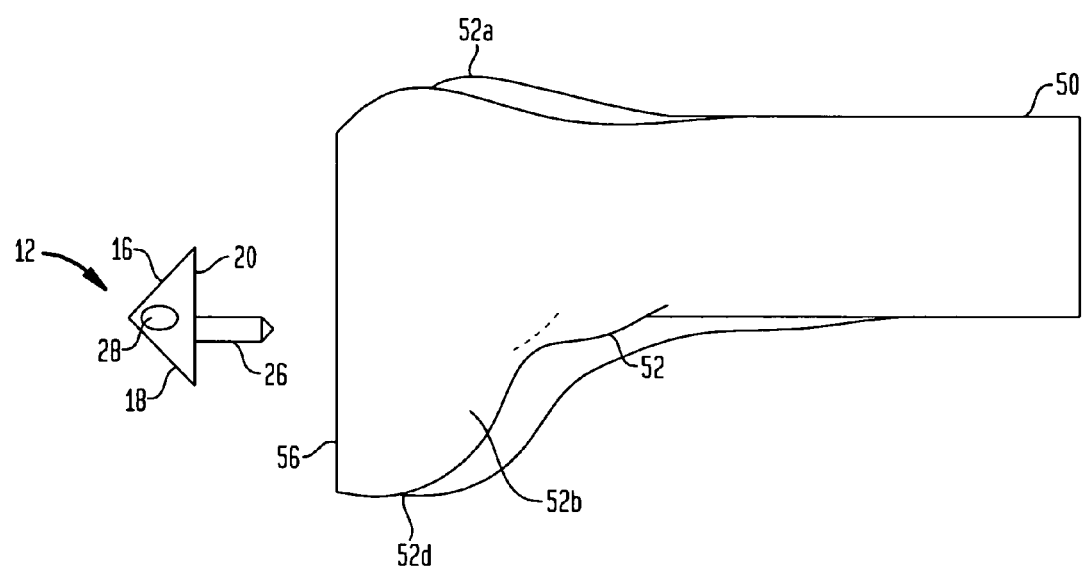

FIG. 9A is an isometric view and FIG. 9B is a medial view showing the first block 12 of the cutting block assembly 10 of FIGS. 1-7 being attached to the distal femur of FIGS. 8A-8B. The first block 12 is advanced toward the distal femur 52 with the contact surface 20 of the first block 12 oriented to face the distal surface 56 of the distal femur. The first block 12 is also oriented with the protrusions 26 of the first block being aligned with the holes 54 of the distal surface 56. In addition, the first block 12 is oriented with the cutting surface 16 (labeled "Anterior") generally facing the anterior portion 52a of the distal femur 52. The first block 12 is advanced toward the distal surface 56 until the protrusions 26 enter the holes 54 of the distal surface 56 and the contact surface 20 of the first block 12 is flush with the distal surface 56, as shown in FIGS. 10A-10B and described further below.

Figure 10A:
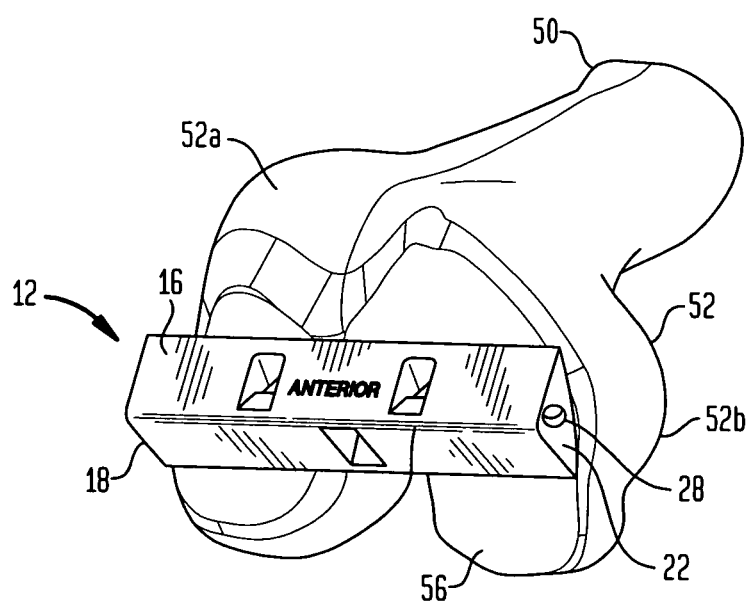

FIG. 10A is an isometric view and FIG. 10B is a medial view showing the first block 12 attached to the distal femur 52 of FIGS. 9A-9B in preparation for making anterior and posterior chamfer cuts on the surface of the distal femur 52. The first surface 16 of the first block 12 provides a guiding surface for making an anterior-chamfer cut along an anterior-chamfer plane 62. To make the anterior-chamfer cut, a bone cutting device such as a saw (not shown) is applied to the surface 16 of the first block 12 and advanced toward the distal surface 56 along the plane 62 until an anterior-chamfer bone portion 64 is removed. In a similar manner, the second surface 18 of the first block 12 provides a guiding surface for making a posterior-chamfer cut along a posterior-chamfer plane 66. To make the posterior-chamfer cut, a cutting device is applied to the surface 18 of the first block 12 and advanced toward the distal surface 56 along plane 66 until a posterior-chamfer bone portion 68 is removed. In one embodiment, holes (not shown) can be made to the distal surface 56 through which pins (not shown) could be inserted through holes 28 of the first block 12 and into the holes of the surface 56. In another embodiment, self-drilling bone pins (not shown) can be used which don't require holes to be predrilled into the surface 56. In both cases, the first block can be more firmly secured to the distal surface 56 which may reduce the possibility of movement of the first block during the cutting process. As explained above, the anterior-chamfer cut is made and then the posterior-chamfer cut is made. However, the sequence of cuts could be reversed with the posterior-chamfer cut being made first and the anterior-chamfer cut being made second.

Figure 11A:
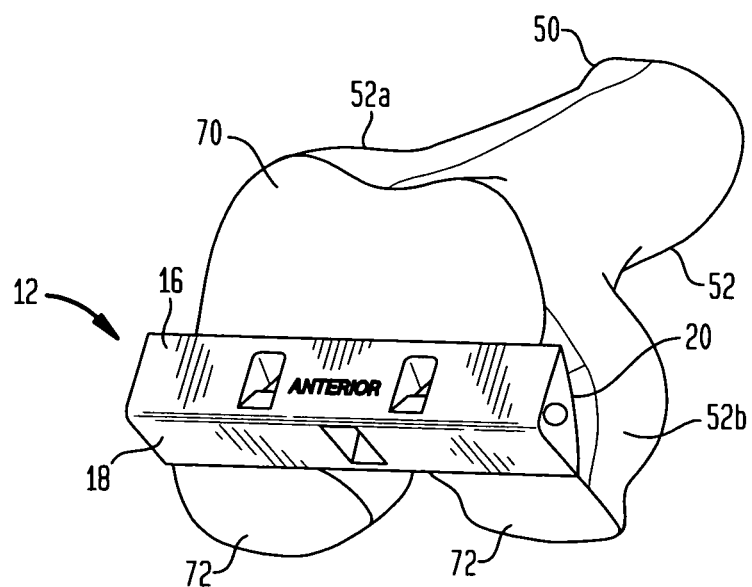
FIG. 11A is an isometric view and FIG. 11B is a medial view showing the distal femur of FIGS. 10A-10B after the anterior and posterior chamfer cuts have been made.
Figure 11B:
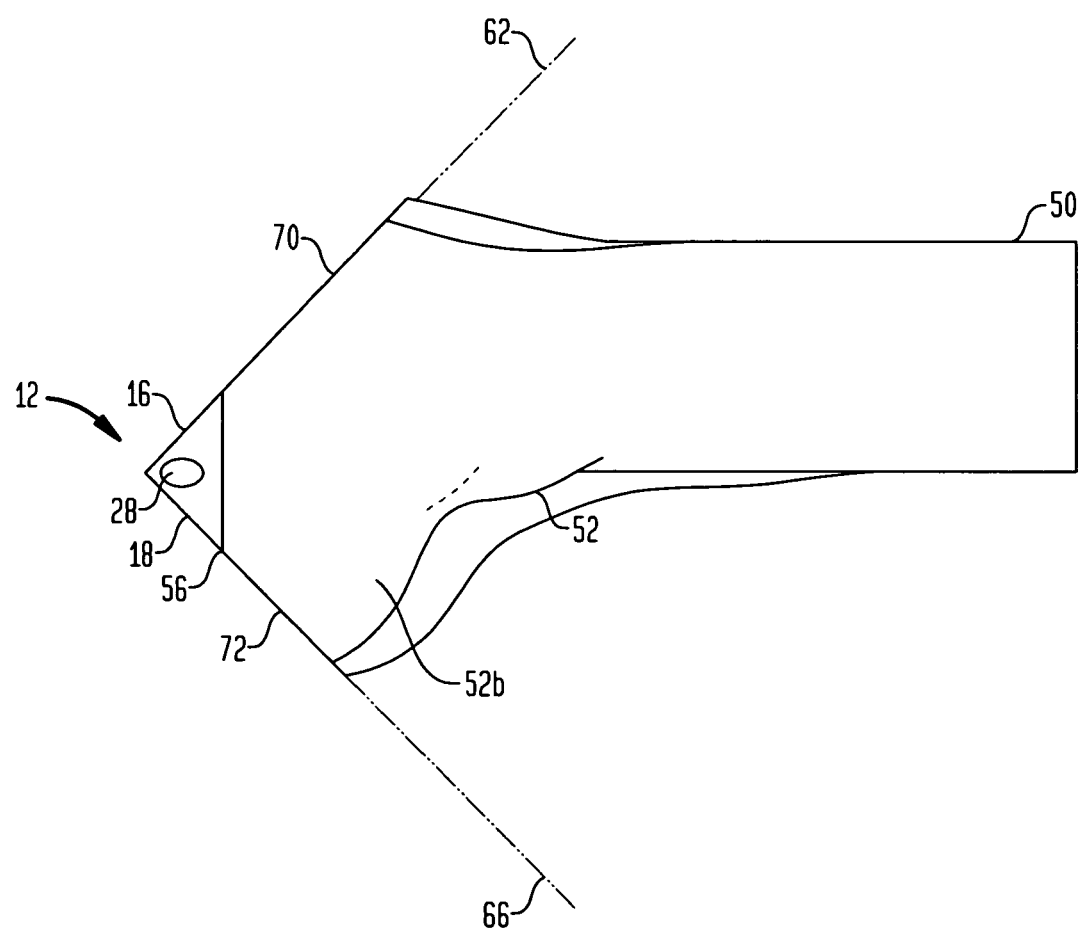

FIG. 11A is an isometric view and FIG. 11B is a medial view showing the distal femur of FIGS. 10A-10B after the anterior and posterior chamfer cuts have been made. Once the anterior-chamfer cut has been made, an anterior-chamfer surface 70 remains. Likewise, once the posterior-chamfer cut has been made, a posterior-chamfer surface 72 remains. The distal femur 52 is now ready to have the second block attached to the first block 12 and to have the anterior and posterior cuts made as shown in FIGS. 12A-12B and explained below.

Figure 12A:
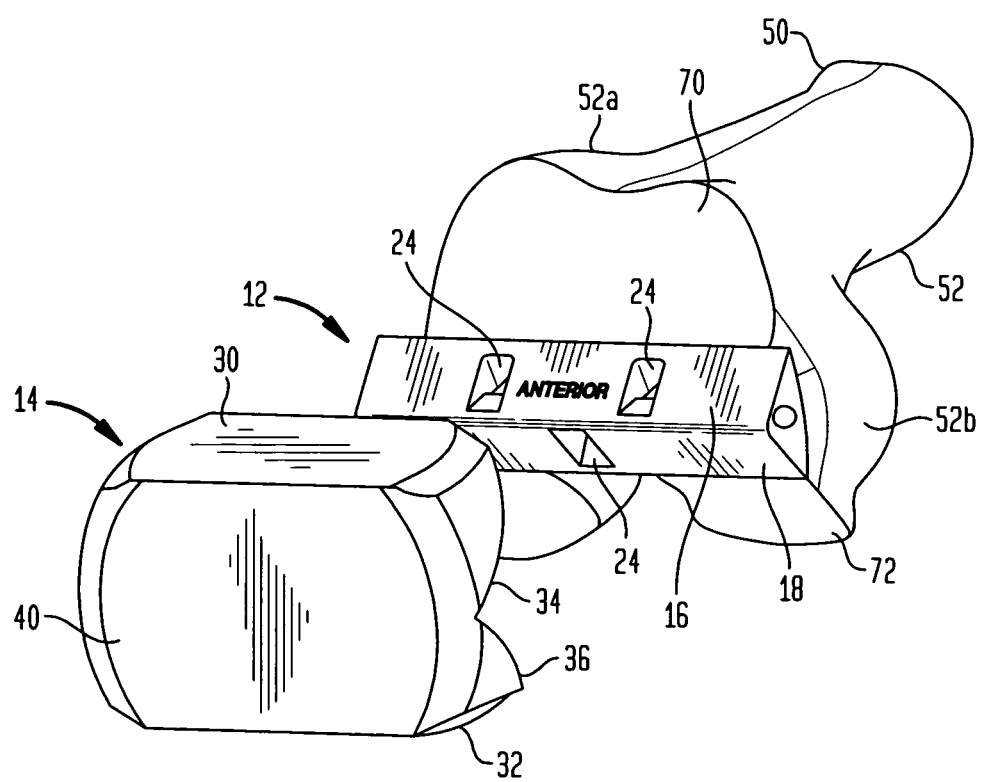
FIG. 12A is an isometric view and FIG. 12B is a medial view showing the distal femur of FIGS. 11A-11B with the second block being attached to the first block.
Figure 12B:
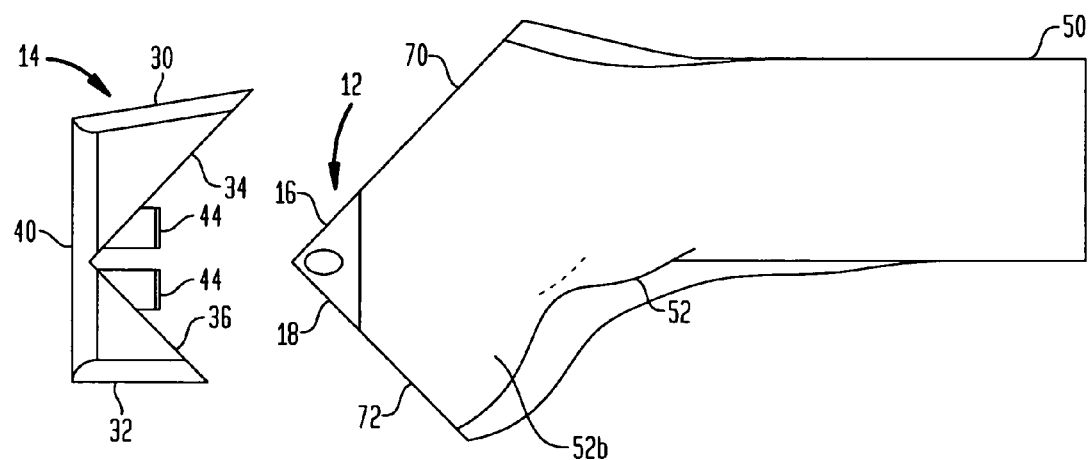

FIG. 12A is an isometric view and FIG. 12B is a medial view showing the distal femur of FIGS. 11A-11B with the second block 14 being attached to the first block 12. The second block 14 is advanced toward the first block 12 with the contact surface 34 of the second block facing the cutting surface 16 of the first block and the contact surface 36 of the second block 14 facing the cutting surface 18 of the first block. The second block 14 is oriented with the protrusions 44 of the second block being aligned with the holes 24 of the first block 12. The second block 14 is then advanced toward the first block 12 until the protrusions 44 of the second block 14 enter the holes 24 of the first block 12 and the blocks interlock, as shown in FIGS. 13A-13B and described further below.

Figure 13A:
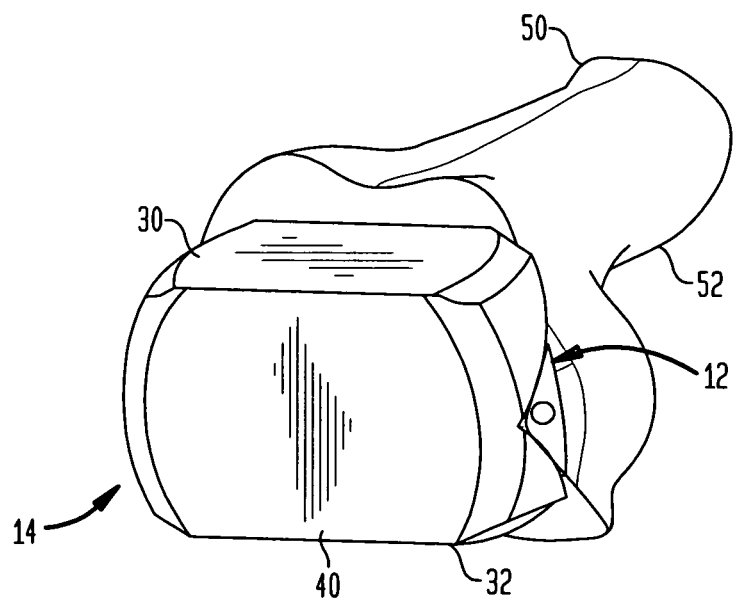
FIG. 13A is an isometric view and FIG. 13B is a medial view showing the first and second blocks being interlocked to form a cutting block assembly for making anterior and posterior cuts on the surface of the distal femur of FIGS. 12A-12B.
Figure 13B:
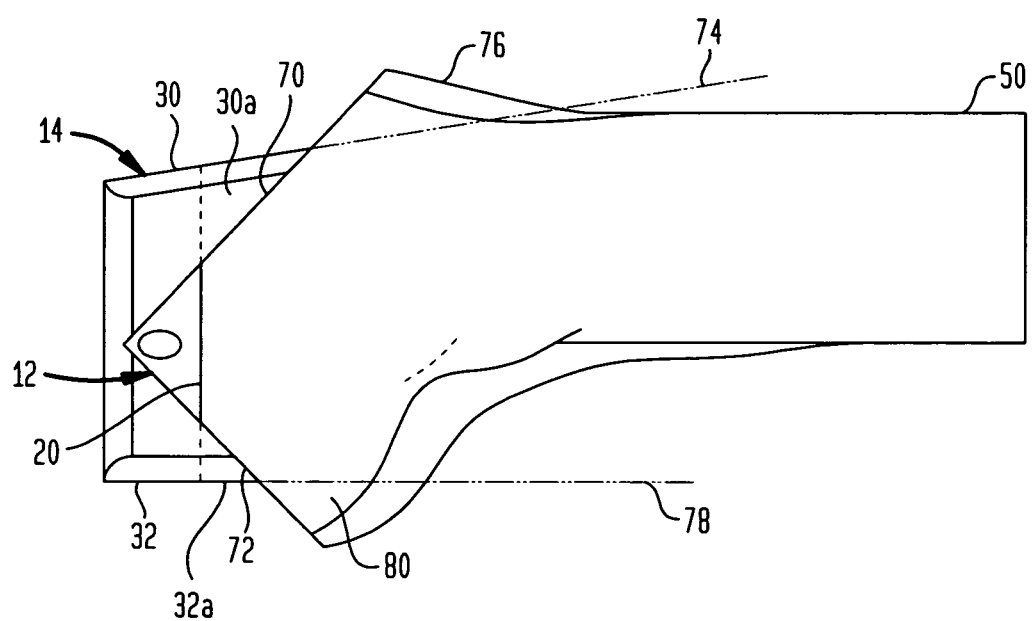

FIG. 13A is an isometric view and FIG. 13B is a medial view showing the first block 12 and second block 14 being interlocked to form a cutting block assembly for making anterior and posterior cuts on the surface of the distal femur 52. As explained above, the cutting assembly 10 has an interlocking feature which allows the blocks 12, 14 to be interlocked to each other and to correlate the four distal femur cuts (anterior-chamfer, posterior-chamfer, anterior, posterior) to each other. In this manner, the accuracy of the cuts may be increased. The anterior cutting surface 30 of the second block 14 provides a guiding surface for making an anterior cut along an anterior plane 74. In a similar manner, the posterior cutting surface 32 of the second block 14 provides a guiding surface for making a posterior cut along a posterior plane 78.

As explained above, the cutting block assembly 10 has a cutting surface verification feature which provides the ability to verify the accuracy of the posterior and anterior chamfer cuts before the anterior and posterior cuts are made. Thus, before the anterior and posterior cuts are made, the second block 14 can be used to check or verify the accuracy of the anterior and posterior chamfer cuts previously made by the first block 12. For example, as explained above, the second block 14 has extended portions 30a, 32a which extend beyond the contact surface 20 and cutting surfaces 16, 18 of the first block 12 and onto the chamfer surfaces 70, 72. The extended portions 30a, 32a provide a user with a visual indication of whether the chamfer surfaces have been properly cut. If any of the chamfer surfaces 70, 72 have been improperly cut, for example, having uneven or skewed surfaces, then a gap or space will be present between the chamfer surfaces and the extended portions 30a, 32a indicating that cuts have been improperly made. In this case, a user can proceed to take remedial action such as reapplying the saw to the chamfer surfaces to attempt to fix the imperfections.

However, if the chamfer surfaces 70, 72 have been properly cut, then no gap or space will be present between the chamfer surfaces and the contact surfaces of the extended portions 30a, 32a indicating that the cuts have been properly made. In this case, a user can proceed to make the anterior and posterior cuts using the second block 14. To make the anterior cut, a bone cutting device is applied to the surface 30 of the second block 14 and advanced toward anterior bone portion 76 and along plane 74 until the anterior bone portion 76 is removed. To make the posterior cut, a cutting device such as a saw is applied to the surface 32 of the second block 14 and advanced toward a posterior bone portion 80 and along surface 78 until the posterior bone portion 80 is removed. In one embodiment, the anterior cut can be made first and the posterior cut can be made second. However, in another embodiment, the posterior cut can be made first and the anterior cut can be made second.

Figure 14A:
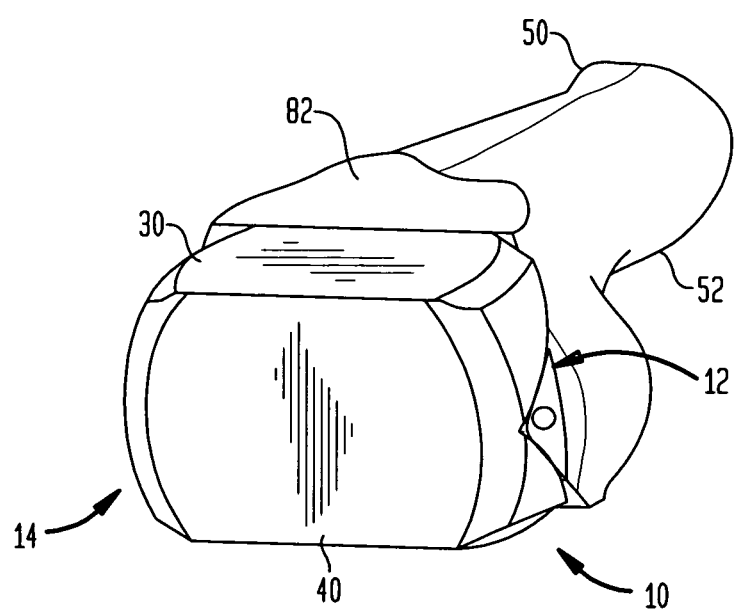
FIG. 14A is an isometric view and FIG. 14B is a medial view showing the distal femur of FIGS. 13A-13B after the anterior and posterior cuts have been made on the surface of the distal femur.
Figure 14B:
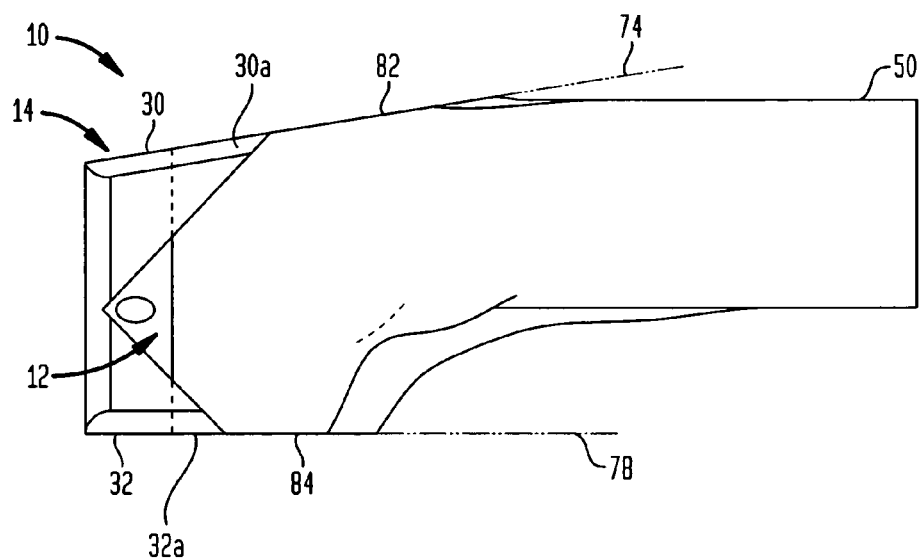

FIG. 14A is an isometric view and FIG. 14B is a medial view showing the distal femur of FIGS. 13A-13B after the anterior and posterior cuts have been made on the surface of the distal femur. As explained above, the extended cutting surfaces 30, 32, which are part of extended portions 30a, 32a, provide increased cutting surface area for making the anterior and posterior cuts. As a result, the accuracy of the anterior and posterior cuts may be improved. Once the anterior cut has been made, an anterior surface 82 remains. Likewise, once the posterior cut has been made, a posterior surface 84 remains. At this point in the surgical procedure, the four cuts (anterior-chamfer, posterior-chamfer, anterior, posterior) have been made and the cutting block assembly 10 can be removed as a single unit from the distal femur as shown in FIG. 15 and explained further below.

Figure 15:
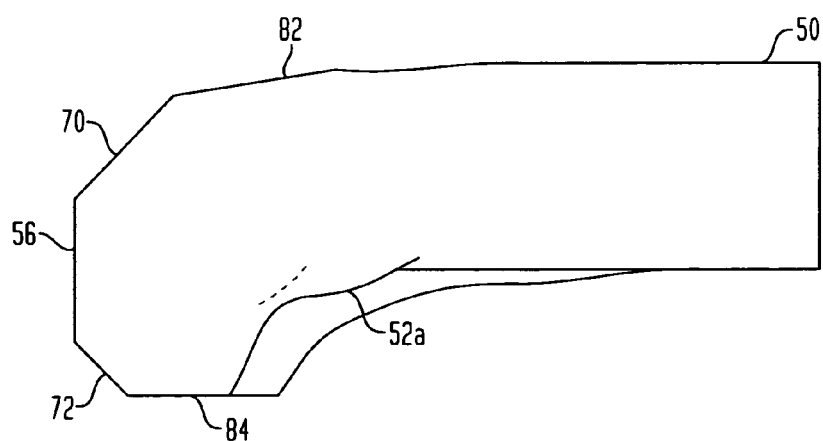
FIG. 15 is a medial view showing the distal femur of FIGS. 14A-14B after the cutting block assembly has been removed.
Figure 16:
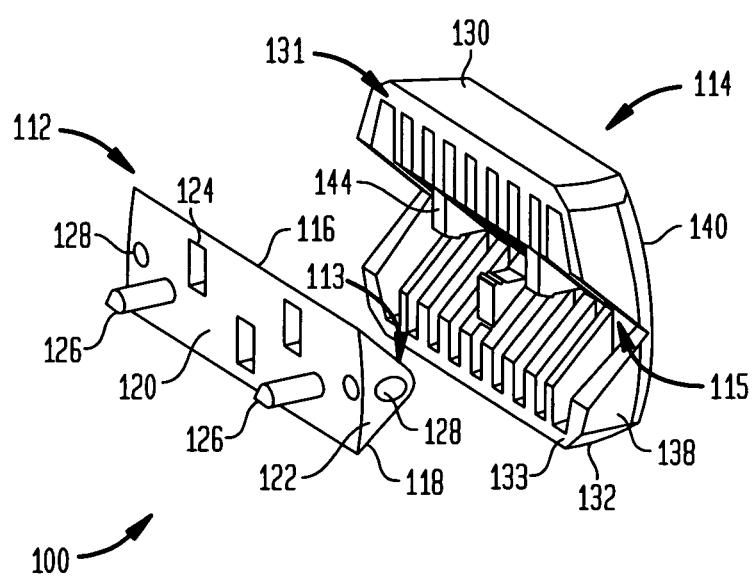
FIG. 16 is an isometric view of the bone cutting blocks in an un-assembled configuration, in accordance with another embodiment of the present application.
Figure 17:
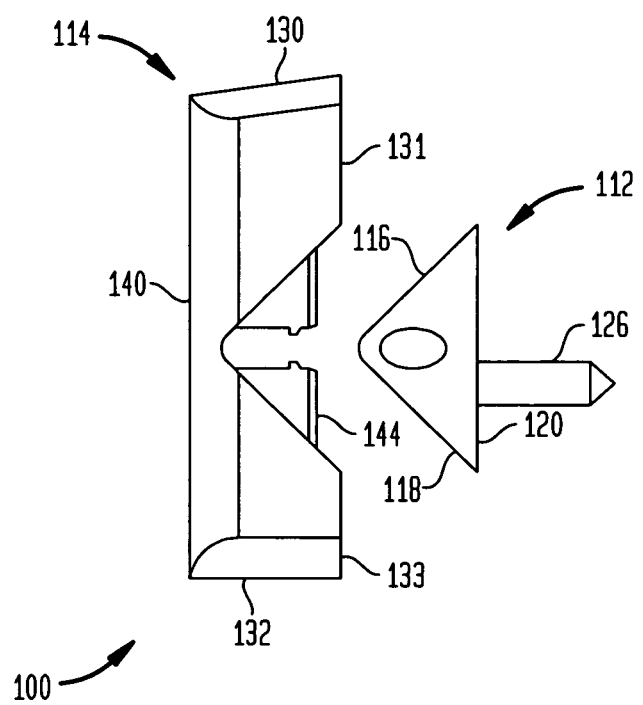
FIG. 17 is a side view of the cutting blocks of FIG. 16.
Figure 18:
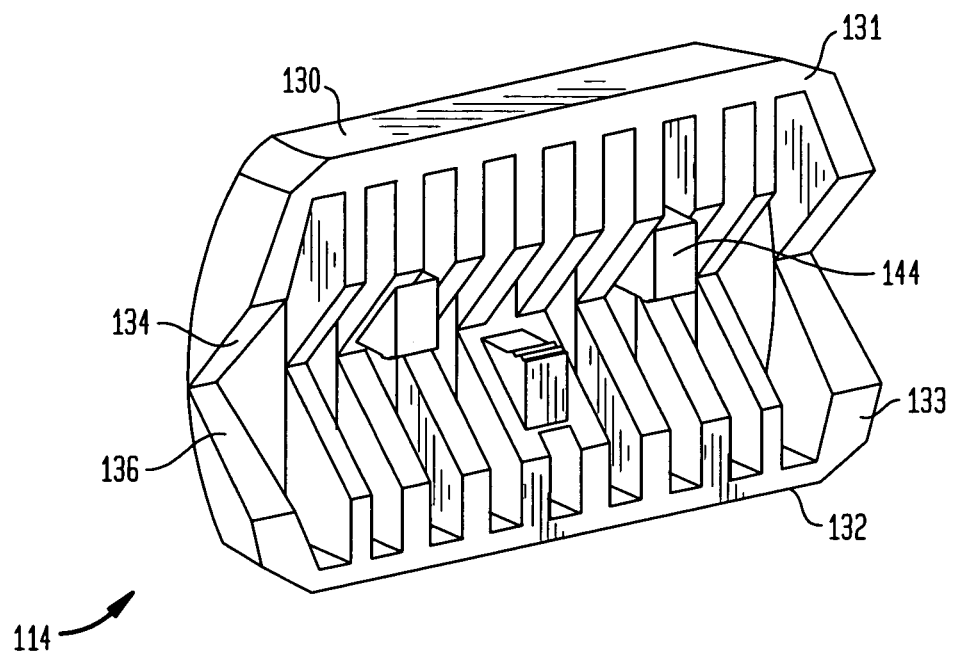
FIG. 18 is an isometric view of the second block of the cutting block assembly of FIG. 16.
Figure 19:
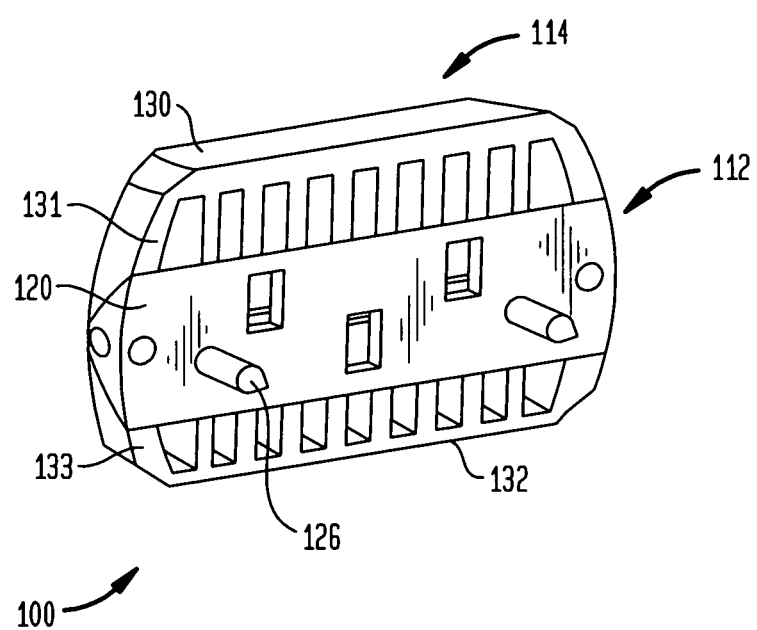
FIG. 19 is an isometric view of the cutting blocks of FIG. 16 in an assembled configuration.
Figure 20:
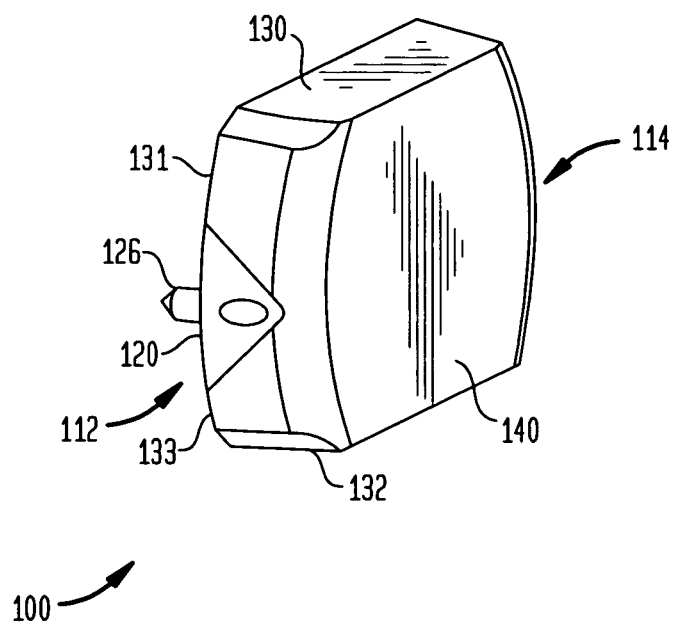
FIG. 20 is another view of the cutting block assembly of FIG. 19.

FIG. 15 is a medial view showing the distal femur 52 after the four cuts have been made and the cutting assembly has been removed. The distal femur 52 shows the four cuts (anterior-chamfer 70, posterior-chamfer 72, anterior 82, posterior 84) and the distal cut 56 made by the cutting block assembly of the present application. The distal femur 52 is now ready for further procedures including the implantation of a knee prosthesis using conventional techniques.

Referring to FIGS. 16-20, shown is a cutting block assembly generally denoted as 100 in accordance with another embodiment of the present invention. The cutting block assembly 100 comprises a first block 112 capable of interlocking with a second block 114 to form a four-in-two (4-in-2) cutting block assembly for resecting a portion of a bone such as a distal femur. The cutting block assembly 100 is similar to the cutting block 10 above. For example, referring to FIGS. 16-20, the first block 112 is a generally triangular shaped block forming an anterior-chamfer cutting surface 116, a posterior-chamfer cutting surface 118, a contact surface 120 and side surfaces 122. The contact surface 120 includes protrusions 126 adapted to fit into holes in the distal femur (not shown). The first block 112 also may include angled pin holes 128 extending outwardly from the contact surface 120 to the side surfaces 122. The second block 114 is a generally trapezoidal shaped block with V-shaped portion 115 sized to receive the V-shaped portion 113 of the first block 112. The second block 114 forms an anterior cutting surface 130, a posterior cutting surface 132, contact surfaces 131, 133 and side surfaces 138. The cutting block assembly 100 has many of the same features as the cutting block 10 above. For example, the cutting block assembly 100 provides an interlocking mechanism for detachably securing the blocks 112, 114 to each other. Also, the cutting block assembly 100 can be made of relatively lightweight material to provide many of the same advantages as in assembly 10.

However, unlike the second block 14 of the cutting block assembly 10 of FIGS. 1-7 above, the second block 114 of the cutting block assembly 100 of FIGS. 16-20 does not include extended portions 30*a*, 32*a*. Instead, the second block 114 includes an anterior contact surface 131 and a posterior contact surface 133. The anterior contact surface 131 is adapted to make contact with the anterior portion of the distal surface of the distal femur (not shown) and the posterior contact surface 133 is adapted to make contact with the posterior portion of the distal surface of the distal femur. In addition, the cutting block assembly 100 can be used for resecting a distal femur similar to the procedure described above in the context of cutting block assembly 10 of FIGS. 1-7, except that the sequence of the cuts is reversed, as explained below in detail. That is, with the cutting block assembly 100, the anterior and posterior cuts are made first and then the anterior and posterior chamfer cuts are made second.

Figure 21:
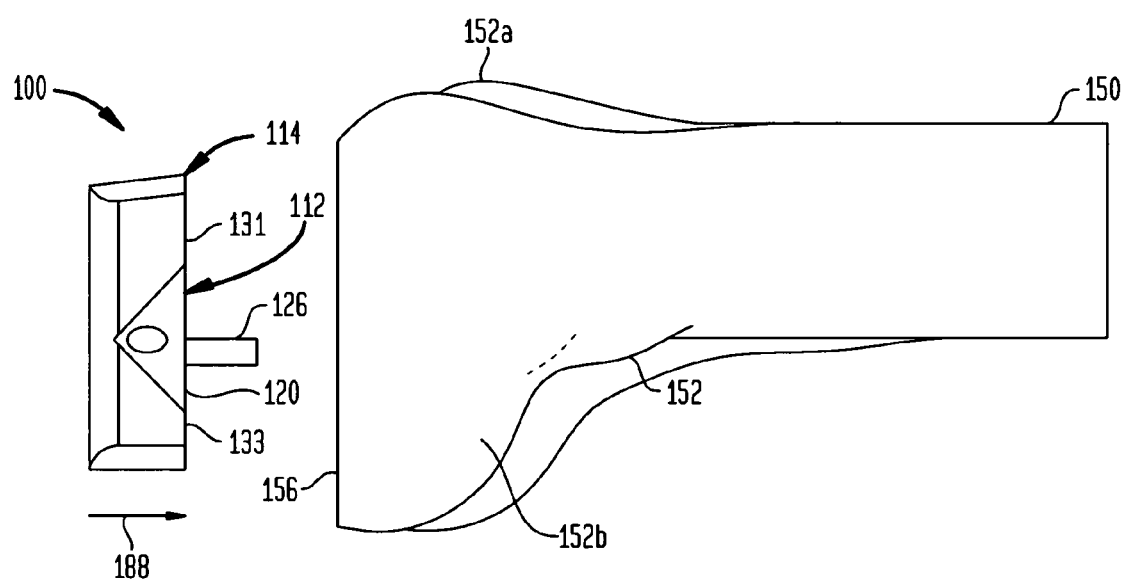
FIG. 21 is a medial view of the cutting block assembly of FIG. 16 being attached to a distal femur.
Figure 22:
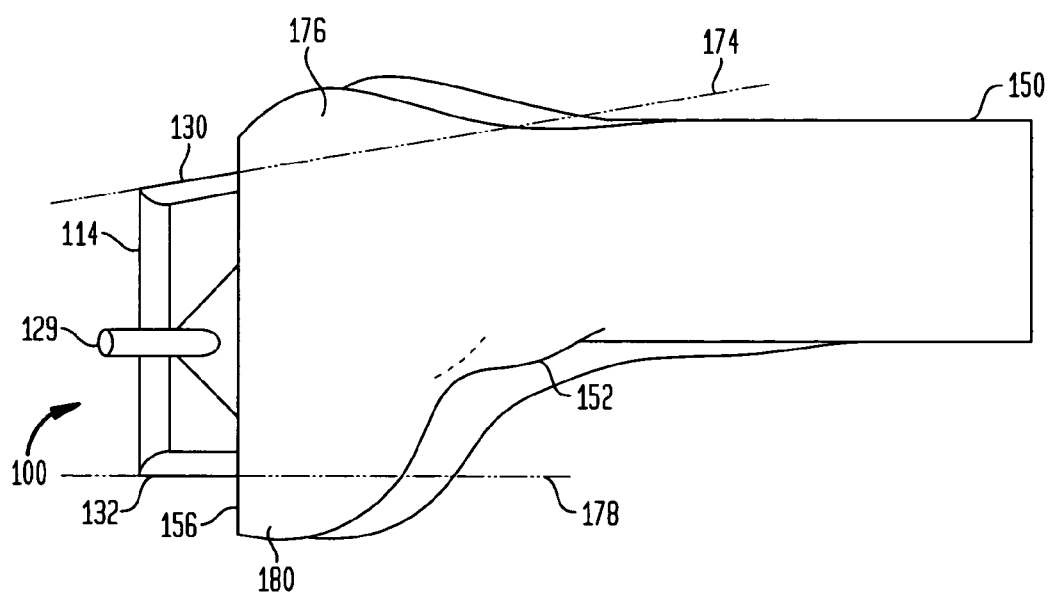
FIG. 22 is a medial view showing the cutting block assembly attached to the distal femur of FIG. 21 in preparation for making anterior and posterior cuts on the surface of the distal femur.

Referring to FIGS. 21-27, a description is provided of a surgical procedure for resecting a distal femur 152 of a femur bone 150 using the cutting block assembly 100 of FIGS. 16-20 in accordance with another embodiment of the present application. This procedure is similar to the procedure explained with reference to FIGS. 9A-9B to 15A-15B in the context of cutting block assembly 10, except that the order of the cuts are reversed and the cutting block assembly 100 is attached to the distal femur as a single unit, as explained below. Referring to FIG. 21, the distal femur 152 has an anterior portion 152*a* and a posterior portion 152*b*. In an initial step of the surgical procedure, a distal cut is made which involves the resection or removal of a distal bone portion (not shown) from the distal femur 152 leaving behind a generally flat resected distal surface 156. Once the distal cut has been made, pilot holes (not shown) can be drilled into the distal surface 156 in precise location and orientation as known to one skilled in the art to accommodate the protrusions 126 of the first block 112. In this embodiment, the first block 112 is attached to the second block to form cutting block assembly 100. In this regard, the cutting block assembly 100 is to be attached to the distal femur as a single unit. The contact surface 120 of the first block 112 is oriented to face the distal surface 156 of the distal femur. The first block 112 is also oriented with the protrusions 126 of the first block being aligned with the holes (not shown) of the distal surface 156. In addition, the second block 114 is oriented with the contact surface 131 facing the anterior portion of the distal surface 156 and the contact surface 133 facing the posterior portion of the distal surface. The cutting block assembly 100 is advanced as a single unit toward the distal surface 156, in the direction shown by arrow 188, until the protrusions 126 enter the holes (not shown) of the distal surface 156 and the contact surface 120 of the first block 112 and the contact surfaces 131, 133 are flush with the distal surface 156, as shown in FIG. 22 and described further below.

FIG. 22 shows the cutting block assembly 100 attached to the distal femur 152 of FIG. 21 in preparation for making anterior and posterior cuts on the surface of the distal femur 152. In one embodiment, pins 129 could be inserted through holes of the first block 112 and into the holes of the distal surface 156 to more firmly secure the assembly 100 to the distal surface 156. The first surface 130 of the second block 114 provides a guiding surface for making an anterior cut along an anterior plane 174. To make the anterior cut, a bone cutting device (not shown) is applied to the surface 130 of the second block 114 and advanced toward the distal surface 156 along the plane 174 until an anterior bone portion 176 is removed. In a similar manner, the second surface 132 of the second block 114 provides a guiding surface for making a posterior cut along a posterior plane 178. To make the posterior cut, a cutting device (not shown) is applied to the surface 132 of the second block 114 and advanced toward the distal surface 156 along plane 178 until a posterior bone portion 180 is removed. In another embodiment, the sequence of cuts could be reversed with the posterior cut being made first and the anterior cut being made second.

Figure 23:
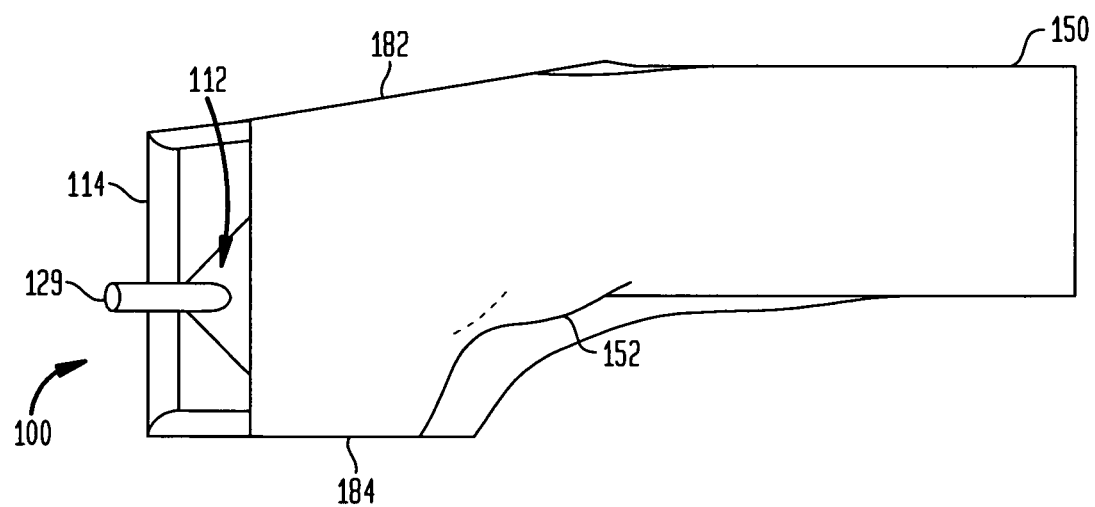
FIG. 23 is a medial view showing the distal femur of FIG. 22 after the anterior and posterior cuts have been made.

FIG. 23 shows the distal femur of FIG. 22 after the anterior and posterior cuts have been made. Once the anterior cut has been made, an anterior surface 182 remains. Likewise, once the posterior cut has been made, a posterior surface 184 remains. The second block 114 can now be detached from the first block 112 in preparation for making the anterior and posterior chamfer cuts as shown in FIG. 24 and explained below.

Figure 24:
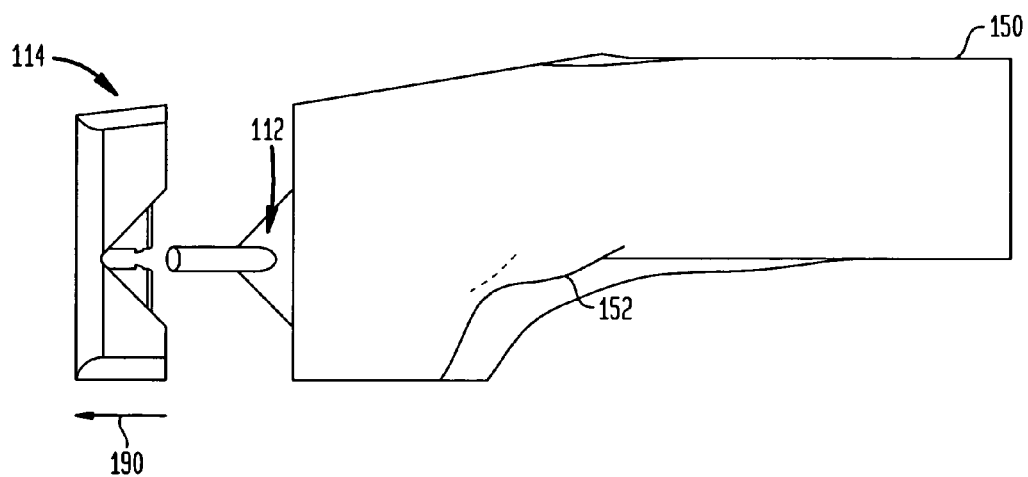
FIG. 24 is a medial view showing the distal femur of FIG. 23 with the second block of the cutting block assembly being removed.

FIG. 24 shows the distal femur of FIG. 23 with the second block 114 being detached from the first block 112. The second block 114 is moved away from the first block 112, in the direction shown by arrow 190, with sufficient force to detach the second block from the first block but with the first block remaining attached to the distal femur. Once the second block 114 has been removed, the distal femur 152 is ready to have the anterior and posterior chamfer cuts made as shown in FIG. 25 and explained below.

Figure 25:
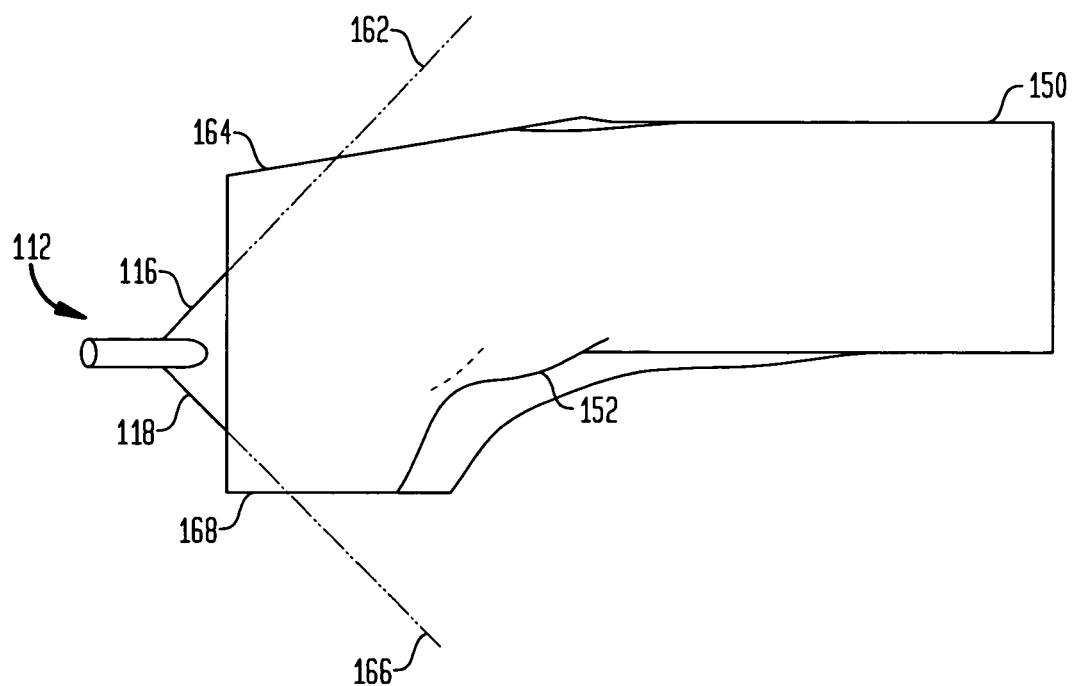
FIG. 25 is a medial view showing the distal femur of FIG. 24 with the second block removed in preparation for making posterior and anterior chamfer cuts on the surface of the distal femur.

FIG. 25 shows the first block 112 attached to the distal femur 152 ready for making anterior and posterior chamfer cuts on the surface of the distal femur 152. The anterior cutting surface 116 of the first block 112 provides a guiding surface for making an anterior-chamfer cut along an anterior plane 162. In a similar manner, the posterior cutting surface 118 of the first block 114 provides a guiding surface for making a posterior-chamfer cut along a posterior plane 166. To make the anterior-chamfer cut, a bone cutting device is applied to the surface 116 of the first block 112 and advanced toward anterior bone portion 164 and along plane 162 until the anterior bone portion 164 is removed. To make the posterior-chamfer cut, a cutting device is applied to the surface 118 of the first block 112 and advanced toward a posterior-chamfer bone portion 168 and along surface 166 until the posterior-chamfer bone portion 168 is removed. In another embodiment, the posterior-chamfer cut can be made first and the anterior-chamfer cut can be made second.

Figure 26:
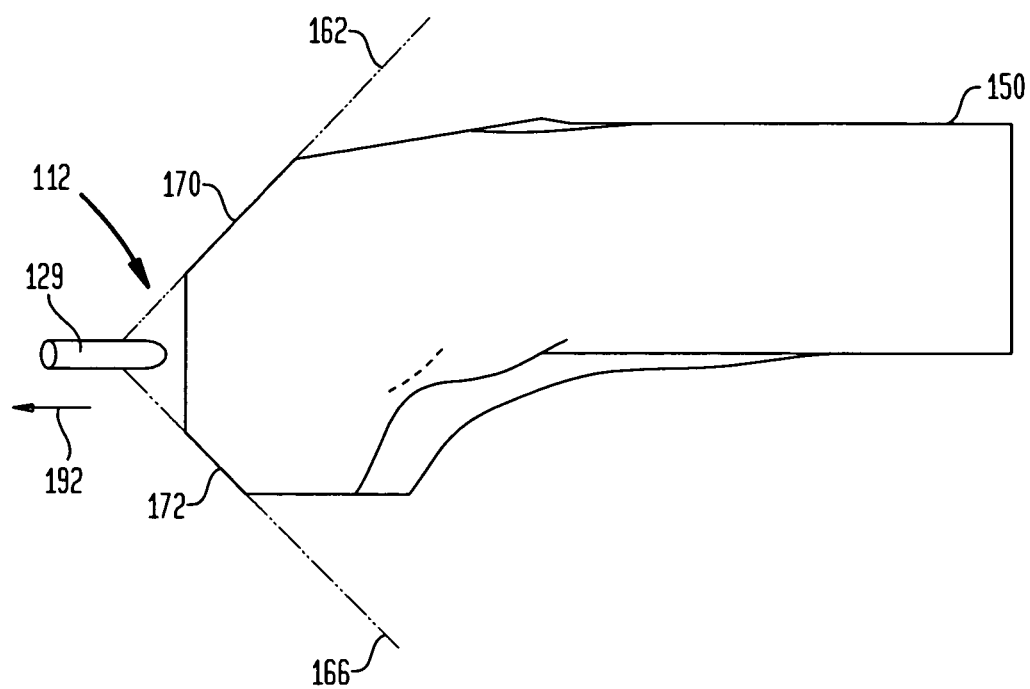
FIG. 26 is a medial view showing the distal femur of FIG. 25 after the anterior and posterior chamfer cuts have been made on the surface of the distal femur.

FIG. 26 shows the distal femur of FIG. 25 after the anterior and posterior chamfer cuts have been made on the surface of the distal femur. Once the anterior-chamfer cut has been made, an anterior-chamfer surface 170 remains. Likewise, once the posterior-chamfer cut have been made, a posterior-chamfer surface 172 remains. At this point in the surgical procedure, the four cuts (anterior-chamfer, posterior-chamfer, anterior, posterior) have been made and the first block 112 can be detached from the distal femur by removing the pins 129 from the first cutting block and distal femur and moving the first block 112 away from the distal femur in the direction shown by arrow 192.

Figure 27:
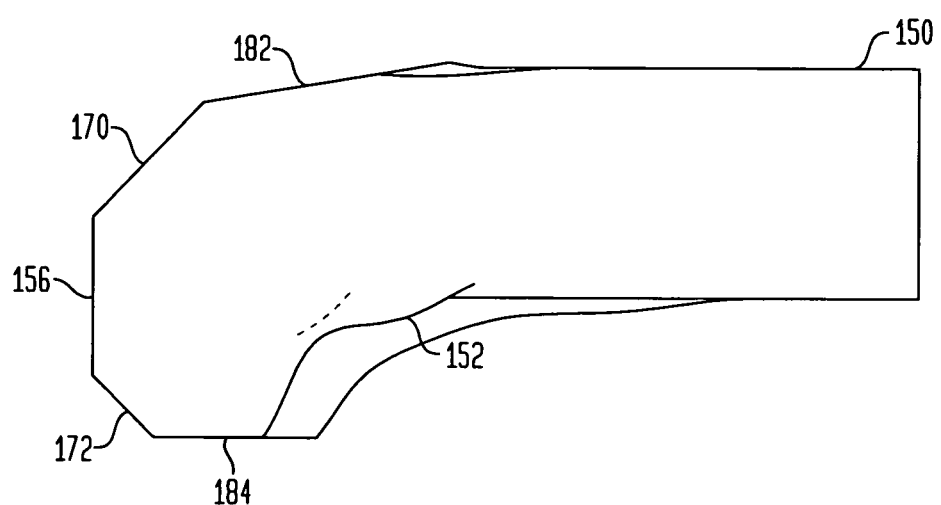
FIG. 27 is a medial view showing the distal femur of FIG. 26 after the first cutting block of the cutting block assembly has been removed and the four cuts have been made.

FIG. 27 shows the distal femur 152 of FIG. 26 after the four cuts have been made and the cutting assembly has been removed. The distal femur 152 shows the distal cut 156 and the four cuts (anterior-chamfer 170, posterior-chamfer 172, anterior 182, posterior 184) made by the cutting block assembly 100 of the present application. The distal femur 152 is now ready for further procedures including the implantation of a knee prosthesis using conventional techniques.

The cutting block devices of the present application may provide various advantages. The cutting block device is a four-in-two (4-in-2) cutting block assembly which may improve accuracy in the preparation of the distal femur for the implantation of a knee prosthesis. The cutting block assembly comprises a first block for making the anterior and posterior chamfer cuts and a second block for making the anterior and posterior cuts. The first and second blocks interlock which may help improve the correlation between the four cuts and improve the accuracy of the cuts. In one embodiment, the second block includes extended surfaces which may help improve the accuracy of the anterior and posterior cuts. In addition the extended surfaces of the second block may help provide a visual indication of the accuracy of the chamfer cuts before the anterior and posterior cuts are made. Moreover, the cutting block can be made of polymeric material which may help reduce the cost of manufacture and may improve the handling of the cutting block during a surgical procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cutting block assembly for resecting a distal femur, the cutting block assembly comprising:
   a first block having:
      a first surface on an anterior side of the first block providing a first guiding surface for making an anterior chamfer cut on the femur; and
      a second surface on a posterior side of the first block providing a second guiding surface for making a posterior chamfer cut on the femur, the second surface being angled with respect to the first surface;
   a second block adapted to detachably couple to the first block, the second block having:
      a first surface on an anterior side of the second block providing a first guiding surface for making an anterior cut on the femur;
      a second surface on a posterior side of the second block providing a second guiding surface for making a posterior cut on the femur;
      a first inferior surface; and
      a second inferior surface angled with respect to the first inferior surface; and
   an interlocking mechanism including:
      one or more protrusions extending from each of the first and second inferior surfaces of the second block on opposite sides of an anterior-posterior axis of the cutting block assembly; and
      one or more holes extending into each of the first and second surfaces of the first block, each of the one or more holes being aligned with one of the one or more protrusions along a superior-inferior axis of the cutting block assembly,
   wherein the second block interlocks with the first block by sliding the one or more protrusions into the one or more holes to securely engage a substantial portion of the first and second guiding surfaces of the first block with a substantial portion of the first and second inferior surfaces of the second block.

2. The cutting block of claim 1 wherein the first block includes an inferior surface having one or more inferior protrusions extending therefrom, the one or more inferior protrusions being sized and spaced to fit into one or more bores extending into one or more surfaces of the distal femur to detachably couple the first block to the distal femur.

3. The cutting block of claim 2 wherein the one or more inferior protrusions are integral to the first block.

4. The cutting block of claim 2 wherein the one or more inferior protrusions are generally cylindrical shaped posts sized and spaced to fit into the one or more bores of the distal femur.

5. The cutting block of claim 1 wherein the first block includes one or more inferior bores for receiving pins to detachably couple the first block to the distal femur.

6. The cutting block of claim 1 wherein the one or more protrusions and the one or more holes of the interlocking mechanism are generally rectangular shaped.

7. The cutting block of claim 1 wherein the one or more protrusions and the one or more holes of the interlocking mechanism are adapted to couple the first and second blocks to each other in a single orientation.

8. The cutting block of claim 1 wherein the one or more protrusions of the interlocking mechanism have at least one ridge on at least one surface of each protrusion and the one or more holes have ramps on at least one surface of each hole, the at least one ridge being adapted to slide over the at least one ramp and to hold the second block in place.

9. The cutting block of claim 1 wherein the first inferior surface of the second block is substantially planar and is substantially parallel to and faces the first guiding surface of the first block and the second inferior surface of the second block is substantially planar and is substantially parallel to and faces the second guiding surface of the first block.

10. The cutting block of claim 9 wherein either the first or second inferior surface of the second block extends beyond either the first or second guiding surface of the first block along a plane generally parallel to either the anterior or posterior chamfer cut to provide a cutting surface verification feature.

11. The cutting block of claim 9 wherein the first and second inferior surfaces of the second block form a generally V-shaped channel and the first and second guiding surfaces of the first block form a generally V-shaped portion, wherein the V-shaped channel is adapted to contact the V-shaped portion.

12. The cutting block of claim 1 wherein the first block is partially solid.

13. The cutting block of claim 1 wherein the second block is partially solid.

14. A cutting block assembly for resecting a distal femur, the cutting block assembly comprising:
   a first block having:
      a first superior surface providing a first guiding surface for making an anterior chamfer cut on the femur;
      a second superior surface angled with respect to the first surface and providing a second guiding surface for making a posterior chamfer cut on the femur; and
      an inferior surface with a plurality of inferior protrusions configured to fit into a plurality of bores extending into at least one surface of the distal femur;
   a second block having:
      an anterior surface providing a first guiding surface for making an anterior cut on the femur;
      a posterior surface providing a second guiding surface for making a posterior cut on the femur;
      a first inferior surface; and
      a second inferior surface angled with respect to the first inferior surface; and a slidable coupling mechanism having:
one or more protrusions with a generally rectangular cross-section extending from each of the first and second inferior surfaces of the second block on opposite sides of an anterior-posterior axis of the assembly; and
one or more holes with a generally rectangular cross-section extending into each of the first and second superior surfaces, each of the one or more holes being aligned with one of the one or more protrusions along a superior-inferior axis of the cutting block assembly,
wherein interlocking the one or more protrusions with the one or more holes securely engages a substantial portion of the first and second guiding surfaces of the first block with a substantial portion of the first and second inferior surfaces of the second block.

15. The cutting block of claim 14 wherein the one or more protrusions each have at least one ridge on at least one surface of each protrusion and the one or more holes each have at least one ramp on at least one surface of each hole, wherein the at least one ridge is adapted to slide over the at least one ramp and to hold the second block in place.

16. The cutting block of claim 14 wherein the first inferior surface of the second block is substantially planar and is substantially parallel to and faces the first superior surface of the first block and the second inferior surface of the second block is substantially planar and is substantially parallel to and faces the second superior surface of the first block.

17. The cutting block of claim 16 wherein the either the first or second inferior surface of the second block extends beyond either the first or second superior surface of the first block along a plane generally parallel to either the anterior or posterior chamfer cut to provide a cutting surface verification feature.

18. The cutting block of claim 16 wherein the first and second inferior surfaces of the second block form a generally V-shaped channel and the first and second superior surfaces of the first block form a generally V-shaped portion, wherein the V-shaped channel is adapted to contact the V-shaped portion.

19. A cutting block assembly for resecting a distal femur, the cutting block assembly comprising:
a first block having:
a first superior guiding surface for making an first anterior chamfer cut on the femur;
a second superior guiding surface for making a first posterior chamfer cut on the femur, the second superior guiding surface being angled with respect to the first superior guiding surface about a medial-lateral axis of the assembly; and
at least one hole on each of the first and second superior guiding surfaces, the holes being on opposite sides of the an anterior-posterior axis of the assembly; and
a second block having:
an anterior guiding surface for making a second anterior cut on the femur;
a posterior guiding surface for making a second posterior cut on the femur;
a first inferior surface proximate to the anterior guiding surface;
a second inferior surface proximate to the posterior guiding surface, the second inferior surface being angled with respect to the first inferior surface about the medial-lateral axis; and
at least one protrusion extending from each of the first and second inferior surfaces, each of the at least one protrusions being aligned with one of the at least one holes along a superior-inferior axis of the cutting block assembly,
wherein sliding the protrusions into the holes securely engages a substantial portion of the first and second superior surfaces with a substantial portion of the first and second inferior surfaces.

20. The cutting block of claim 19 wherein each of the at least one protrusions has at least one ridge on at least one surface of each protrusion and each of the at least one holes has at least one ramp on at least one surface of each hole, wherein the at least one ridge is adapted to slide over the at least one ramp and to hold the second block in place.

* * * * *